United States Patent [19]

Chemla

[11] Patent Number: 5,714,599
[45] Date of Patent: Feb. 3, 1998

[54] PROCESS FOR THE PREPARATION OF STE SPECIFIC 1'-SPIRO-NUCLEOSIDES

[75] Inventor: Philippe Chemla, Mulhouse, France

[73] Assignee: Novartis Corporation, Summit, N.J.

[21] Appl. No.: 265,297

[22] Filed: Jun. 24, 1994

[51] Int. Cl.$^6$ .................. C07H 31/70; C07D 498/08
[52] U.S. Cl. ............ 536/55.3; 536/28.6; 536/28.7; 536/28.8; 536/27.22; 544/1; 544/63; 544/65; 548/300.7; 548/301.4
[58] Field of Search ............... 536/28.6, 28.7, 536/28.8, 27.22, 55.3; 544/1, 63, 65; 548/300.7, 301.4

[56] References Cited

U.S. PATENT DOCUMENTS

| | | | |
|---|---|---|---|
| 4,952,234 | 8/1990 | Haneishi et al. | 536/28.8 |
| 5,064,760 | 11/1991 | Haneishi et al. | 536/28.8 |

FOREIGN PATENT DOCUMENTS

| | | |
|---|---|---|
| 4129616 | 3/1992 | Germany. |
| 4129728 | 3/1992 | Germany. |

OTHER PUBLICATIONS

Matsumoto et al., Tetrahedron Letters, vol. 34, No. 39, pp. 6289–6292 (1993).
Derwent Abstract of JP 2167283, #90–242014/32.
Chem. Abst. 114:81826, Mizukai et al., p. 78.
Trends Pharm. Sci., vol. 11, pp. 198–205 (1990), DeClercq.
Ann. Rep. Med. Chem. 25, pp. 149–158 (1990), D. Norbeck.
Adv. Heterocycl. Chem. vol. 8, pp. 115–142 (1967), J. Pliml et al.
J. Org. Chem., vol. 39, No. 25, pp. 3654–3660 (1974), Niedballa et al.
Chem. Ber. 114, 1234–1255 (1981) (Abstract in English language on front page), Vorbrüggen et al.
J. Org. Chem., vol. 58, No. 4, pp. 807–808, M. Jung et al (1993).
Angew. Chem., Int. Edit. Engl., vol. 14, No. 6, pp. 471–472, H. Vurbrüggen (1975).
J. Org. Chem., vol. 41, No. 10, pp. 1836–1846, E. Prisbe et al (1976).
Tetrahedron, vol. 47, No. 12.13, pp. 2111–2120, 2133–2144, 2145–2154, Mio et al, (1991).
J. Chem. Soc., 325, pp. 1632–1635, Y. Knobler et al (1958).
J. Org.Chem., vol. 23, pp. 1257–1261, C. Mosher et al (1958).
Tetrahedron Letters, vol. 25, No. 4, pp. 395–398, Wilcox et al (1984).
Synthesis, pp. 682–684, Grochowski et al (1976).
Synthesis, pp. 1031–1032, Kaskar et al (1990).
Synthesis, pp. 933–934, Liv et al (1991).
Helv. Chim. heta, vol. 65, Fasc. S, Nr. 136., pp. 1404–1411, Tronchet et al (1982) (Abstract in English language on front page).
Z. Chem., 4, pp. 303–304 (1964) (Abstract in English language enclosed).
Chem. Ber. 101, pp. 2559–2567, Huisgen et al (1968) (Abstract in English language enclosed).
Tetrahedron, vol. 41, No. 17, pp. 3455–3462, Wovkulich et al (1985).
Tetrahedron Letters, vol. 27, No. 27, pp. 3119–3122, Evans et al (1986).
Tetrahedron Letters, No. 48, pp. 4763–4766, Kock et al (1978).
Tetrahedron Letters, vol. 31, No. 23, pp. 3351–3354, Cicchi et al (1990).
J. Org. Chem., vol. 33, No. 3, pp. 1219–1225, M. Stout et al (1968).
Tetrahedron Letters, vol. 34, No. 39, pp. 6289–6292, Matsumoto et al (1993).
Tetrahedron Letters, vol. 34, No. 46, pp. 7391–7394, P. Chemla (1993).
Protective Groups in Organic Synthesis, 2nd Ed., Editors T. W. Greene and P. G. M. Wuts, John Wiley & Sons, Inc., New York (1991).
J. Org. Chem., vol. 39, No. 17, pp. 2644–2646, Pless (1974).
Synthesis, pp. 1–28, O. Mitsunobu (1981).
Synthesis, p. 413, Castro et al. (1977).
Tetrahedron Letters, vol. 30, No. 16, pp. 2045–2048, Bako et al (1989).
J. Org. Chem., vol. 40, No. 23, pp. 3376–3378, Abushanab et al (1975).
Chemistry Letters, Chem. Soc. of Japan, pp. 1001–1002, T. Yoshimura et al (1983).
Bull Chem. Soc. Japan, 58, pp. 1413–1420, M. Yamaura et al (1985).
Tetrahedron Letters, vol. 31, No. 23, pp. 3351–3354, S. Cicchi et al, (1990).
Helvetica Chimica Acta, vol. 46, Fasc. 3, No. 85, pp. 766–780, Testa et al (1963) (Abstract in English language enclosed).
J. Org. Chem., vol. 45, No. 10, pp. 1920–1924, C. Phillips et al (1980).
Synthesis, E. Marvell et al, pp. 457–467 (1973).
Tetrahedron Letters, No. 36, pp. 4273–4278, J. Pappas et al (1966).
J. Org. Chem., vol. 26, pp. 2525–2528, M. Newman et al (1961).

(List continued on next page.)

*Primary Examiner*—James O. Wilson
*Attorney, Agent, or Firm*—Marla J. Mathias; William T. Teoli, Jr.

[57] ABSTRACT

The invention relates to a novel process for stereocontrolled preparation of 1',1'-disubstituted and 1'-spiro-nucleosides of the formula I $$\text{HO---CH}_2 \quad \quad \quad \text{NH---R}_9 \qquad (I)$$
$$\diagdown \text{O} \diagup$$
$$\diagdown \quad \diagup \text{R}_8$$
$$\text{A}$$

in which the substituents A, $R_8$ and $R_9$ are as defined in claim 1, and to novel intermediates and their use in this process and to processes for the preparation of the novel intermediates. The process is illustrated by the example of biologically active (+)-hydantocidin.

38 Claims, No Drawings

OTHER PUBLICATIONS

J. Am. Chem. Soc., vol. 89, No. 10, pp. 2416–2423, J. Albright et al (1967).

J. Org. Chem., vol. 55, No. 1, pp. 270–275, J. Chung et al (1990).

Tetrahedron, vol. 34, pp. 1651–1660, K. Omura et al (1978).

Derwent Abstract of JP 2085287, #90–136472/18.

J. Org. Chem., vol. 45, pp. 1175–1176, Kraus et al (1980).

J. Org. Chem., vol. 33, No. 7, pp. 2822–2827, M. Winkley et al. (1968).

PROCESS FOR THE PREPARATION OF STE SPECIFIC 1'-SPIRO-NUCLEOSIDES

The present invention relates to a novel process for stereocontrolled preparation of 1',1'-disubstituted and 1'-spiro-nucleosides, and to novel intermediates and their use in this process and to processes for the preparation of the novel intermediates.

Structurally modified nucleosides such as 2'-deoxyribonucleosides and, in particular, nucleosides substituted stereospecifically on the anomeric 1'-carbon atom of the sugar component, such as N-β-ribonucleosides, are potentially interesting pharmaceutical and agricultural active ingredients. This is known, for example, from Trends Pharm. Sci. 11, 198 (1990) and Ann. Rep. Med. Chem. 25, 149 (1990).

There is therefore a great interest in the simplest possible processes for their preparation.

The stereocontrolled synthesis of β-substituted nucleosides is essentially carried out by two methods, that is to say by the Hilbert-Johnson reaction described in Adv. Heterocycl. Chem. 8, 115 (1967) and the Vorbrüggen modification of the Hilbert-Johnson reaction known from J. Org. Chem. 39 (25), 3654 (1974) and Chem. Bet. 114, 1234 (1981). In the Hilbert-Johnson reaction, 2,4-dialkoxy-pyrimidines react with protected sugar derivatives halogenated on the anomeric 1'-carbon atom to give, almost exclusively, 1'-β-pyrimidine nucleosides. In the Hilbert-Johnson reaction modified by Vorbrüggen, 2,4-disilyloxy-pyrimidines react with protected sugar derivatives which are O-acetyl- and O-methyl-substituted on the anomeric 1'-carbon atom in the presence of Friedel-Crafts catalysts to give, almost exclusively, 1-β-pyrimidine nucleosides. In both methods, the necessary preconditions for the formation of the β-substituted pyrimidine nucleosides exist when dialkoxy- or disilyloxy-pyrimidine bases and reactive 1'-halogenated or 1'-O-acetyl- or 1'-O-methyl-substituted sugars having an α-terminal acyloxy group on the 2'-carbon atom react with one another, since, according to Acta Chemica Scandinavica B 38,367 (1984), the 2'-acyloxy group in fact stabilizes the intermediately formed planar anomeric 1'-carbon cation from the α-side and thus directs the halogen- or O-acetyl- or O-methyl-substituting dialkoxy- or disilyloxy-pyrimidine base into the β-position of the sugar. Without this α-terminal 2'-acyloxy group on the sugar, a racemic mixture of α- and β-anomeric nucleotides would always be formed.

An intramolecular Vorbrüggen coupling is now used for the first time in J. Org. Chem. 58, 807 (1993) to solve the synthesis problem of the configuration on the anomeric 1'-carbon atom in the case of 2'-deoxy-sugar molecules. In this reaction, the sugar employed is 3-O-methylribal, which can be prepared from D-ribose via 6 stages, and the base employed is a pyrimidinone, which has to be silylated on the oxygen atom before the Vorbrüggen coupling. A mixture of two products is formed in the process, that is to say the desired coupling product and the hydrolysis product.

This process is not yet satisfactory in respect of the purity and yield of the end products, accessibility of the starting compounds and reaction procedure, and furthermore is limited with respect to the derivatives which can be formed from the sugar and nucleoside base moieties.

The object of the present invention is thus to propose a process which is essentially free from such disadvantages.

According to the invention, the object is achieved in that, as the key step, the intramolecular Vorbrüggen coupling according to Chem. Ber. 114, 1234 (1981) and Angew. Chem., Int. Ed. Engl., 14, 421 (1975) is modified to form an oxygen-nitrogen bridge between the 5'-$CH_2$ group and the anomeric 1'-carbon atom. The configuration of the nucleoside formed (glycosylation) is thereby determined by the configuration of the carbon atom carrying the —$CH_2$—O—NH—$R_9$ group in the 4'-position of the compound of the formula XI below by formation of the bicyclic isoxazolidine of the formula XII.

The present invention thus relates to a process for the preparation of compounds of the formula I

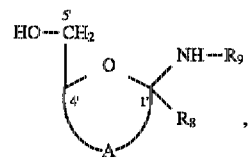

in which

A is the group

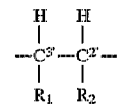

or —CH=CH—;

$R_1$ is hydrogen, halogen, hydroxyl, $C_1$–$C_4$alkoxy, $C_1$–$C_4$alkoxy-$C_1$–$C_4$alkoxy, tri-$C_1$–$C_6$alkylsilyloxy, benzyloxy or phenoxy which are unsubstituted or substituted by $C_1$–$C_4$alkyl, $C_1$–$C_4$haloalkyl, halogen, cyano or nitro, $R_{10}$—C(O)—O—, $R_3(R_4)N$—,

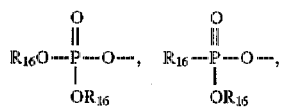

azido, cyano or $L_1$—O—, wherein $L_1$ is a protective group;

$R_2$ is hydrogen, halogen, hydroxyl, $C_1$–$C_4$alkoxy, $C_1$–$C_4$alkoxy-$C_1$–$C_4$alkoxy, tri-$C_1$–$C_6$alkylsilyloxy, benzyloxy or phenoxy which are unsubstituted or substituted by $C_1$–$C_4$alkyl, $C_1$–$C_4$haloalkyl, halogen, cyano or nitro, $R_{10}$—C(O)—O—, $R_3(R_4)N$—, azido, cyano or $L_1$—O—, wherein $L_1$ is a protective group, with the proviso that only one of the substituents $R_1$ or $R_2$ is azido; or $R_1$ together with $R_2$ is —OSi($R_{11}$)$R_{20}$O— or —OC($R_{12}$)$R_{21}$O—;

$R_3$ is hydrogen, unsubstituted or substituted $C_1$–$C_{10}$alkyl, $C_3$–$C_{10}$alkenyl or $C_3$–$C_{10}$alkynyl, formyl, $C_1$–$C_{10}$alkylcarbonyl which is unsubstituted or substituted by halogen, hydroxyl, $C_1$–$C_4$alkoxy, $C_1$–$C_4$alkylamino, di-$C_1$–$C_4$alkylamino, cyano, $C_1$–$C_4$alkoxycarbonyl, carbamoyl, $C_1$–$C_4$alkylaminocarbonyl, di-$C_1$–$C_4$alkylaminocarbonyl or phenyl, $C_3$–$C_{10}$alkenylcarbonyl, $C_3$–$C_{10}$alkynylcarbonyl, $C_1$–$C_{10}$alkoxycarbonyl or phenoxycarbonyl or benzyloxycarbonyl which are unsubstituted or substituted by halogen, $C_1$–$C_4$alkyl, $C_1$–$C_4$haloalkyl, $C_1$–$C_4$alkoxy or $C_1$–$C_4$haloalkoxy;

$R_4$ is hydrogen, unsubstituted or substituted $C_1$–$C_{10}$alkyl, $C_3$–$C_{10}$alkenyl or $C_3$–$C_{10}$alkynyl, formyl, $C_1$–$C_{10}$alkylcarbonyl which is unsubstituted or substituted by halogen, hydroxyl, $C_1$–$C_4$alkoxy, $C_1$–$C_4$alkylamino, di-$C_1$–$C_4$alkylamino, cyano, $C_1$–$C_4$alkoxycarbonyl, carbamoyl, $C_1$–$C_4$alkylaminocarbonyl, di-$C_1$–$C_4$alkylaminocarbonyl or phenyl, $C_3$–$C_{10}$alkenylcarbonyl, $C_3$–$C_{10}$alkynylcarbonyl, $C_1$–$C_{10}$alkoxycarbonyl or phenoxycarbonyl or benzyloxycarbonyl which are unsubstituted or substituted by halogen, $C_1$–$C_4$alkyl, $C_1$–$C_4$haloalkyl, $C_1$–$C_4$alkoxy or $C_1$–$C_4$haloalkoxy;

with the proviso that only one of the substituents $R_3$ or $R_4$ is formyl; or $R_3$ together with $R_4$ is —$(CH_2)_n$—, —$(CH_2)_o$—O—$(CH_2)_p$—, —$(CH_2)_o$—S—$(CH_2)_p$— or —$(CH_2)_o$—NH—$(CH_2)_p$—, which can be unsubstituted or substituted by $C_1$–$C_4$alkyl;

n is 4, 5 or 6;

o is 1, 2, 3 or 4;

p is 1, 2, 3 or 4; and the sum of o and p is 3, 4 or 5;

$R_{10}$ is hydrogen, $C_1$–$C_4$alkyl or benzyl or phenyl which are unsubstituted or substituted by $C_1$–$C_4$alkyl, $C_1$–$C_4$alkoxy, $C_1$–$C_4$haloalkyl, halogen or cyano;

$R_{11}$ is $C_1$–$C_4$alkyl or phenyl;

$R_{20}$ is $C_1$–$C_4$alkyl; or $R_{11}$ together with $R_{20}$ is —$(CH_2)_{n3}$—;

$R_{12}$ is hydrogen, $C_1$–$C_4$alkyl or phenyl;

$R_{21}$ is hydrogen or $C_1$–$C_4$alkyl; or $R_{12}$ together with $R_{21}$ is —$(CH_2)_{n3}$—;

$n_3$ is 4, 5 or 6;

$R_8$ is unsubstituted or substituted $C_1$–$C_{10}$alkyl, $C_2$–$C_{10}$alkenyl, $C_2$–$C_{10}$alkynyl, $C_1$–$C_{10}$alkyl-C(Q)—, $C_2$–$C_{10}$alkenyl-C(Q)—, $C_2$–$C_{10}$alkynyl-C(Q)—, $C_2$–$C_{10}$alkenyloxycarbonyl, $C_2$–$C_{10}$alkynyloxycarbonyl, phenoxycarbonyl or benzyloxycarbonyl, cyano, carboxyl, phenyl, nitro, $C_1$–$C_{10}$alkoxycarbonyl, $R_3(R_4)$N—C(O)— or $L_2$—NH—$C_1$–$C_{10}$alkyl, wherein $L_2$ is a protective group;

$R_9$ is hydrogen, unsubstituted or substituted $C_1$–$C_{10}$alkyl, $C_2$–$C_{10}$alkenyl, $C_2$–$C_{10}$alkynyl, $C_1$–$C_{10}$alkyl-C(Q)—, $C_2$–$C_{10}$alkenyl-C(Q)—, $C_2$–$C_{10}$alkynyl-C(Q)—, phenyl, benzyl, phenyl-C(Q)—, phenoxycarbonyl, benzyloxycarbonyl, phenoxycarbonyl-$C_1$–$C_{10}$alkyl or benzyloxycarbonyl-$C_1$–$C_{10}$alkyl, $C_1$–$C_4$alkoxycarbonyl, $C_1$–$C_4$alkoxy-C(O)—NH—SO_2—, $NH_2$—$SO_2$—, $R_{18}(R_{19})$N—C(Q)—, $R_3(R_4)$N—C(O)-$C_1$–$C_{10}$alkyl, $C_1$–$C_4$alkoxy-NH—C(O)—, phenoxy-NH—C(O)— or benzyloxy-NH—C(O)—; or $R_8$ and $R_9$ together form a ring —X—Y—Z—, in which X is the groups $C_1$–$C_3$alkeylene,

wherein the alkylene chain can be unsubstituted or substituted by halogen, hydroxyl, $C_1$–$C_4$alkoxy, amino, $C_1$–$C_4$alkylamino, di-$C_1$–$C_4$alkylamino, cyano, carboxyl, $C_1$–$C_4$alkoxycarbonyl, $C_1$–$C_4$alkylcarbonyloxy, carbamoyl, $C_1$–$C_4$alkylaminocarbonyl, di-$C_1$–$C_4$alkylaminocarbonyl or phenyl;

Q is oxygen or sulfur;

Y is oxygen, $C_1$— or $C_2$-alkylene which is unsubstituted or substituted by $C_1$–$C_4$alkyl or —$NR_5$—;

Z is the groups $C_1$–$C_3$alkylene,

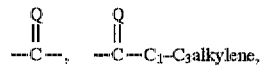

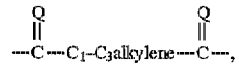

wherein the alkylene chain can be unsubstituted or substituted by halogen, hydroxyl, $C_1$–$C_4$alkoxy, amino, $C_1$–$C_4$alkylamino, di-$C_1$–$C_4$alkylamino, cyano, carboxyl, $C_1$–$C_4$alkoxycarbonyl, carbamoyl, $C_1$–$C_4$alkylaminocarbonyl, di-$C_1$–$C_4$alkylaminocarbonyl or phenyl,

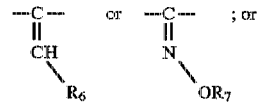

Y and Z together are a group

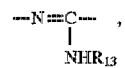

wherein bonding to the ring C atom takes place via the C atom;

$R_5$ is hydrogen, unsubstituted or substituted $C_1$–$C_{10}$alkyl, $C_3$–$C_{10}$alkenyl, $C_3$–$C_{10}$alkynyl, $C_3$–$C_{10}$alkenylcarbonyl or $C_3$–$C_{10}$alkynylcarbonyl, formyl, $C_1$–$C_{10}$alkylcarbonyl which is unsubstituted or substituted by halogen, hydroxyl, $C_1$–$C_4$alkoxy, amino, $C_1$–$C_4$alkylamino, di-$C_1$–$C_4$alkylamino, cyano, $C_1$–$C_4$alkoxycarbonyl, carbamoyl, $C_1$–$C_4$alkylaminocarbonyl, di-$C_1$–$C_4$alkylaminocarbonyl or phenyl, $C_1$–$C_{10}$alkoxycarbonyl or phenoxycarbonyl, benzylcarbonyl, benzyloxycarbonyl or phenyl which are unsubstituted or substituted by halogen, $C_1$–$C_4$alkyl, $C_1$–$C_4$haloalkyl, $C_1$–$C_4$alkoxy or $C_1$–$C_4$haloalkoxy;

$R_6$ is unsubstituted or substituted $C_1$–$C_{10}$alkyl, carboxyl, $C_1$–$C_4$alkoxycarbonyl, carbamoyl, $C_1$–$C_4$alkylaminocarbonyl or di-$C_1$–$C_4$alkylaminocarbonyl;

$R_7$ is hydrogen, $C_3$–$C_7$cycloalkyl or unsubstituted or substituted $C_1$–$C_{10}$alkyl, $C_2$–$C_{10}$alkenyl, $C_3$–$C_{10}$alkynyl or benzyl;

$R_{13}$ is hydrogen or unsubstituted or substituted $C_1$–$C_{10}$alkyl, $C_1$–$C_{10}$alkylcarbonyl, phenyl or benzyl;

$R_{16}$ is $C_1$–$C_5$alkyl, $C_3$–$C_5$alkenyl, phenyl or benzyl;

$R_{18}$ is unsubstituted or substituted $C_1$–$C_{10}$alkyl, $C_1$–$C_{10}$alkoxycarbonyl, phenoxycarbonyl, benzyl, benzyloxycarbonyl, $C_1$–$C_6$alkylcarbonyl, $C_1$–$C_4$alkylaminocarbonyl, di-$C_1$–$C_4$alkylaminocarbonyl or $L_2$; and $R_{19}$ is hydrogen, formyl, $C_1$–$C_{10}$alkylcarbonyl which is unsubstituted or substituted by halogen, hydroxyl, $C_1$–$C_4$alkoxy, amino, $C_1$–$C_4$alkylamino, di-$C_1$–$C_4$alkylamino, cyano, carboxyl, $C_1$–$C_4$alkoxycarbonyl, carbamoyl, $C_1$–$C_4$alkylaminocarbonyl, di-$C_1$–$C_4$alkylaminocarbonyl or phenyl, $C_3$–$C_{10}$alkenylcarbonyl, $C_3$–$C_{10}$alkynylcarbonyl, $C_1$–$C_{10}$alkoxycarbonyl, phenoxycarbonyl, benzyl, benzyloxycarbonyl, $C_1$–$C_4$alkylaminocarbonyl, di-$C_1$–$C_4$alkylaminocarbonyl or $L_2$,
and salts of these compounds, which comprises
a) cyclizing the compound of the formula XI

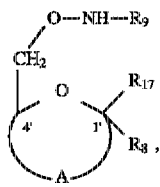 (XI)

in which

A, $R_8$ and $R_9$ are defined, but A is other than

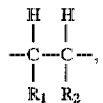

if $R_1$ and $R_2$ simultaneously are hydroxyl or $H_2N$— and with the exception of $R_8$ and $R_9$ together forming a ring —X—Y—Z—, $R_7$ is halogen, hydroxyl, $C_1$–$C_{10}$alkoxy, unsubstituted or substituted $C_1$–$C_{10}$alkyl-C(O)O—, benzyloxy or benzoyloxy, $CF_3C(O)O$—, $C_1$–$C_{10}$alkoxy-C(O)O—, $C_1$–$C_6$alkylsulfonyloxy, phenylsulfonyloxy, $CF_3S(O)_2$O— or a group $L_1$—O—,
wherein $L_1$ is a protective group; or $R_{17}$ and $R_8$ together form a group

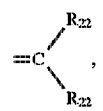

=N—O$R_7$, —O—CH($R_6$)— or —O—C($R_{12}$)$R_{21}$—O—CH$_2$—; and the radicals $R_{22}$ independently of one another are fluorine, chlorine, bromine, unsubstituted or substituted $C_1$–$C_{10}$alkyl, carboxyl, $C_1$–$C_4$alkoxycarbonyl, carbamoyl, $C_1$–$C_4$alkylaminocarbonyl or di-$C_1$–$C_4$alkylaminocarbonyl; into the compound of the formula XII

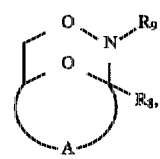 (XII)

in which

A, $R_8$ and $R_9$ are as defined, and subsequently $b_1$) splitting the N—O bond in the compound of the formula XII by hydrogenolysis or with an organometallic compound to give 1',1'-disubstituted nucleotides of the formula I, or $b_2$) first cyclizing the compound of the formula XII, in which $R_8$ and $R_9$ are as defined, with the exception of $C_1$–$C_{10}$alkyl, $C_2$–$C_{10}$alkenyl, $C_2$–$C_{10}$alkynyl, phenyl or benzyl, to give the compound of the formula XIII

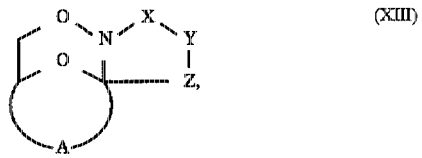 (XIII)

in which

A, X, Y and Z are as defined, in a manner known per se, and subsequently splitting the N—O bond by hydrogenolysis or with an organometallic compound (in accordance with $b_1$)) to give 1'-spiro-nucleosides of the formula I.

In the above definitions, halogen is to be understood as meaning fluorine, chlorine, bromine and iodine, preferably fluorine, chlorine and bromine.

The alkyl, alkenyl and alkynyl groups can be straight-chain or branched, which also applies to the alkyl, alkenyl and alkynyl moiety of haloalkyl, alkoxyalkyl, alkylsulfonyloxy, alkylcarbonyloxy-alkyl, benzoyloxy-alkyl, alkyl-C(Q), alkenyl-C(Q), alkynyl—C(Q)—, alkenyloxycarbonyl, alkynyloxycarbonyl, haloalkenyl, haloalkynyl, trialkylsilyloxy, alkoxycarbonyl-alkyl and phenoxycarbonyl-alkyl groups.

Examples of alkyl groups are methyl, ethyl, n-propyl, iso-propyl, n-butyl, iso-butyl, sec-butyl, tert-butyl and the various isomeric pentyl, hexyl, heptyl, octyl, nonyl and decyl radicals. These alkyl groups can be substituted by halogen, hydroxyl, $L_1$—O—, $L_2$—NH—, where $L_1$ and $L_2$ are a protective group, $C_1$–$C_4$alkoxy, amino, $C_1$–$C_4$alkylamino, di-$C_1$–$C_4$alkylamino, cyano, nitro, carboxyl, $C_1$–$C_4$alkoxycarbonyl, $C_1$–$C_4$alkylcarbonyloxy, benzoyloxy, benzyloxy, carbamoyl, $C_1$–$C_4$alkylaminocarbonyl, di-$C_1$–$C_4$alkylaminocarbonyl or phenyl.

Examples of alkenyl groups are vinyl, allyl, methallyl, 1-methylvinyl, but-2-en-1-yl, pentenyl, 2-hexenyl and 3-heptenyl, preferably alkenyl radicals having a chain length of 3 to 5 carbon atoms. $C_3$–$C_{10}$alkenyl groups can be substituted on the saturated carbon atoms by hydroxyl, $L_1$—O—, $L_2$—NH—, where $L_1$ and $L_2$ are a protective group, $C_1$–$C_4$alkoxy, amino, $C_1$–$C_4$alkylamino, di-$C_1$–$C_4$alkylamino, cyano, nitro, carboxyl, $C_1$–$C_4$alkoxycarbonyl, $C_1$–$C_4$alkylcarbonyloxy, benzoyloxy, benzyloxy, carbamoyl, $C_1$–$C_4$alkylaminocarbonyl, di-$C_1$–$C_4$alkylaminocarbonyl or phenyl. The $C_2$–$C_{10}$alkenyl groups can be substituted on saturated or unsaturated carbon atoms by halogen.

Examples of alkynyl groups are ethynyl, propargyl, 3-butynyl, but-2-yn-1-yl, 1-methylpropargyl, 1-pentynyl, pent-4-yn-1-yl or 2-hexynyl, preferably ethynyl, propargyl and 1-methylpropargyl. The $C_3$–$C_{10}$alkynyl groups can be substituted on the saturated carbon atoms by halogen, hydroxyl, $L_1$—O—, $L_2$—NH—, where $L_1$ and $L_2$ are a protective group, $C_1$–$C_4$alkoxy, amino, $C_1$–$C_4$alkylamino, di-$C_1$–$C_4$alkylamino, cyano, nitro, carboxyl, $C_1$–$C_4$alkoxycarbonyl, $C_1$–$C_4$alkylcarbonyloxy, benzoyloxy, benzyloxy, carbamoyl, $C_1$–$C_4$alkylaminocarbonyl, di-$C_1$–$C_4$alkylaminocarbonyl or phenyl.

The alkyl, alkenyl and alkynyl substituents mentioned can be chosen freely. They have no influence on the feasibility of the present process for the preparation of the compounds of the formula I.

In those cases where 1'-spiro-nucleosides of the formula I in which $R_8$ and $R_9$ together form a ring —X—Y—Z— are to be prepared, however, certain prerequisites of the functionalities of the substituents $R_8$ and $R_9$ must be met, so that $R_8$ and $R_9$ can form a ring —X—Y—Z— in accordance with process variant $b_2$)—$b_1$) in equation 1. For example, $R_8$ and $R_9$ must be other than $C_1$–$C_{10}$alkyl, $C_2$–$C_{10}$alkenyl, $C_2$–$C_{10}$alkynyl, phenyl or benzyl.

Haloalkyl groups are alkyl groups which are mono- or polysubstituted, in particularly mono- to trisubstituted, by halogen, where halogen is, specifically, iodine and, in particular, fluorine, chlorine and bromine, for example fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl.

Cyanoalkyl is, for example, cyanomethyl, cyanoethyl, cyanoeth-1-yl and cyanopropyl.

Hydroxyalkyl is, for example, hydroxymethyl, 2-hydroxyethyl and 3-hydroxypropyl.

Aminoalkyl is, for example, aminomethyl, aminoethyl, aminoeth-1-yl and aminopropyl. Carboxyalkyl is, for example, carboxymethyl, carboxyethyl, carboxyeth-1-yl and carboxypropyl.

Alkoxyalkyl is, for example, methoxymethyl, ethoxymethyl, propoxymethyl, methoxyethyl, ethoxyethyl, propoxyethyl, butoxyethyl, methoxypropyl, ethoxypropyl or propoxypropyl.

Haloalkenyl groups are alkenyl groups which are mono- or polysubstituted by halogen, where halogen is bromine, iodine and, in particular, fluorine and chlorine, for example 3-fluoropropenyl, 3-chloropropenyl, 3-bromopropenyl, 2,3,3-trifluoropropenyl, 2,3,3-trichloropropenyl and 4,4,4-trifluoro-but-2-en-1-yl. Among the $C_2$–$C_{10}$alkenyl radicals which are substituted by 1,2 or 3 halogen atoms, those which have a chain length of 3 to 5 carbon atoms are preferred.

Alkoxy is, for example, methoxy, ethoxy, n-propoxy, iso-propoxy, n-butoxy, iso-butoxy, sec-butoxy, tert-butoxy, and the isomeric pentyloxy, hexyloxy, heptyloxy, octyloxy, nonyloxy and decyloxy radicals.

Alkoxycarbonyl is, for example, methoxycarbonyl, ethoxycarbonyl, n-propoxycarbonyl, iso-propoxycarbonyl and n-butoxycarbonyl, preferably methoxycarbonyl and ethoxycarbonyl.

Alkylamino is, for example, methylamino, ethylamino and the isomeric propyl- and butylamino.

Dialkylamino is, for example, dimethylamino, diethylamino and the isomeric dipropyl- and dibutylamino.

The cycloalkyl radicals which can be substituents are, for example, cyclopropyl, cyclobutyl, cyclopentyl, cyclohexyl or cycloheptyl.

Alkoxyalkoxy is, for example, methoxymethoxy, ethoxymethoxy, ethoxyethoxy, propoxymethoxy, propoxyethoxy, propoxypropoxy, butoxyethoxy and butoxybutoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy.

Phenyl or benzyl, also as a component of a substituent, such as phenoxy, benzyloxy, benzoyloxy, phenoxycarbonyl, benzyloxycarbonyl or phenylsulfonyloxy, is unsubstituted or substituted. The substituents can then be in the ortho-, meta- or para-position. Preferred substituent positions are the ortho- and para-position to the ring linkage point.

Substituents are, for example, $C_1$–$C_4$alkyl, halogen, $C_1$–$C_4$haloalkyl, cyano, nitro, hydroxyl, $C_1$–$C_4$alkoxy, $C_1$–$C_4$haloalkoxy, amino, $C_1$–$C_4$alkylamino, di-$C_1$–$C_4$alkylamino, carboxyl, $C_1$–$C_4$alkoxycarbonyl, carbamoyl, $C_1$–$C_4$alkylaminocarbonyl or di-$C_1$–$C_4$alkylaminocarbonyl.

$L_1$ and $L_2$, for example in the definition of the radicals $R_1$, $R_2$, $R_8$ and $R_{17}$ or as $L_1$—O— or $L_2$—NH-substituents on alkyl, alkenyl and alkynyl radicals, are oxygen- or nitrogen-protective groups, as described, for example, in "Protective Groups in Organic Synthesis", 2nd Edition, Editors Th. W. Greene and P. G. M. Wuts, John Wiley & Sons, Inc., New York, 1991.

Preferred oxygen-protective groups $L_1$ are, for example, methoxymethyl (MOM), methylthiomethyl (MTM), methoxyethoxymethyl ether (MEM), benzyl (Bn), benzoyl (Bz), acetyl (Ac), allyl, p-methoxybenzyl (PMB), trialkylsilyl, mesitoate (2,4,6-trimethylbenzoate) and for diols, carbonates.

Preferred nitrogen-protective groups $L_2$ are, for example, benzyloxycarbonyl (CBZ), tert-butyloxycarbonyl (BOC), toluene-4-sulfonyl (tosyl), benzyl (Bn), p-methoxybenzyl (PMB) and acetyl (Ac).

The substituents in composite definitions, for example alkylcarbonyl, alkoxycarbonyl, alkylaminocarbonyl, dialkylaminocarbonyl, phenoxycarbonylalkyl, benzyloxycarbonylalkyl and dialkylaminoalkyl, can also be defined correspondingly.

The salts of the compounds of the formula I with acid hydrogen, in particular the derivatives with carboxylic acid groups (for example carboxyl-substituted alkyl, alkenyl and alkynyl groups; $R_3$ and $R_4$ are carboxyl-substituted alkoxycarbonyl; $R_5$ is carboxyl-substituted alkylcarbonyl; $R_6$ and $R_8$ are carboxyl; $R_9$ is the group $R_{18}(R_{19})N$—C(Q)—, where $R_{18}$ is carboxyl or $R_{19}$ is carboxyl or carboxyl-substituted alkylcarbonyl, or the group alkoxy-C(O)—NH—SO$_2$—; or $R_{17}$ and $R_8$ together are a group $$=C\begin{matrix}R_{22}\\ \\R_{22}\end{matrix}$$

or =N—OR$_7$, where $R_{22}$ is carboxyl and $R_7$ is hydrogen; or X and Z are the groups $C_1$–$C_3$alkylene $$-\overset{\underset{\|}{Q}}{C}-C_1-C_3\text{alkylene or } -\overset{\underset{\|}{Q}}{C}-C_1-C_3\text{alkylene}-\overset{\underset{\|}{Q}}{C}-,$$

where the alkylene chain is substituted by carboxyl) are, for example, alkali metal salts, for example sodium and potassium salts; alkaline earth metal salts, for example calcium and magnesium salts; ammonium salts, i.e. unsubstituted ammonium salts and mono- or polysubstituted ammonium salts, for example triethylammonium and methylammonium salts; or salts with other organic bases.

Preferred alkali metal and alkaline earth metal hydroxides as salt-forming agents are, for example, the hydroxides of lithium, sodium, potassium, magnesium or calcium, but in particular those of sodium or potassium.

Examples of amines which are suitable for ammonium salt formation are both ammonia and primary, secondary and tertiary $C_1$–$C_{18}$alkylamines, $C_1$–$C_4$hydroxyalkylamines and $C_2$–$C_4$alkoxyalkylamines, for example methylamine, ethylamine, n-propylamine, iso-propylamine, the four isomeric butylamines, n-amylamine, iso-amylamine, hexylamine, heptylamine, octylamine, nonylamine, decylamine, pentadecylamine, hexadecylamine, heptadecylamine, octadecylamine, methyl-ethylamine, methyl-iso-propylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, di-iso-propylamine, di-n-butylamine, di-n-amylamine, di-iso-amylamine, dihexylamine, diheptylamine, dioctylamine, ethanolamine, n-propanolamine, iso-propanolamine, N,N-diethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine, propylenediamine, trimethylamine, triethylamine, tri-n-propylamine, tri-iso-propylamine, tri-n-butylamine, tri-iso-butylamine, tri-sec-butylamine, tri-n-amylamine, methoxyethylamine and ethoxyethylamine; heterocyclic amines, for example pyridine, quinoline, iso-quinoline, morpholine, thiomorpholine, N-methylmorpholine, N-methyl-thiomorpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but in particular triethylamine, iso-propylamine and di-iso-propylamine.

The compounds of the formula I can be in the form of optical isomers (enantiomers or diastereomers). The stereochemistry on the 11'- and 4'-positions plays an essential role in the process according to the invention for stereocontrolled preparation of 1',1'-disubstituted and 1'-spironucleosides of the formula I. Further centres of asymmetry are present in the 2'- and 3'-positions. The present invention relates to all these optical isomer combinations. The compounds of the formula I according to the invention moreover can also contain further centres of asymmetry (for example in the substituents $R_1$, $R_2$, $R_8$ and $R_9$), which likewise are also included in their individual combinations. The invention thus relates to all the enantiomers and diastereomers which can be deduced from the formula I.

If an aliphatic C=C or C=N—O double bond (syn/anti) is present, geometric isomers may occur. The present invention also relates to these isomers.

The process according to the invention is preferably carried out for compounds of the formula I, in which A is the group

$R_1$ is hydroxyl, $C_1$–$C_4$alkoxy, $C_1$–$C_4$alkoxy-$C_1$–$C_4$alkoxy, trimethylsilyloxy, tert-butyl-dimethylsilyloxy or benzyloxy or phenoxy which are unsubstituted or substituted by $C_1$–$C_4$alkyl, $C_1$–$C_4$haloalkyl, halogen, cyano or nitro; $R_{10}$—C(O)—O—,

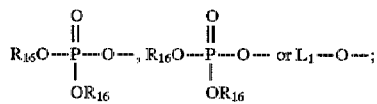

$R_2$ is hydroxyl, $C_1$–$C_4$alkoxy, $C_1$–$C_4$alkoxy-$C_1$–$C_4$alkoxy, trimethylsilyloxy, tert-butyl-dimethylsilyloxy, benzyloxy or phenoxy which are unsubstituted or substituted by $C_1$–$C_4$alkyl, $C_1$–$C_4$haloalkyl, halogen, cyano or nitro, $R_{10}$—C(O)—O— or $L_1$—O—; or $R_1$ together with $R_2$ is —OSi($R_{11}$)$R_{20}$O— or —OC($R_{12}$)$R_{21}$O—;

$R_3$ is hydrogen, unsubstituted $C_1$–$C_{10}$alkyl, $C_1$–$C_{10}$alkylcarbonyl, $C_1$–$C_{10}$alkoxycarbonyl, phenoxycarbonyl or benzyloxycarbonyl;

$R_4$ is hydrogen or unsubstituted $C_1$–$C_{10}$alkyl;

$R_{10}$ is $C_1$–$C_4$alkyl or benzyl or phenyl which are unsubstituted or substituted by $C_1$–$C_4$alkyl, $C_1$–$C_4$alkoxy, $C_1$–$C_4$haloalkyl, halogen or cyano;

$R_{11}$ is $C_1$–$C_4$alkyl or phenyl;

$R_{20}$ is $C_1$–$C_4$alkyl;

$R_{12}$ is hydrogen or $C_1$–$C_4$alkyl;

$R_{21}$ is $C_1$–$C_4$alkyl;

$R_8$ is $C_1$–$C_{10}$alkyl, $C_2$–$C_{10}$alkenyl, $C_2$–$C_{10}$alkynyl, $C_1$–$C_{10}$alkyl-C(Q)—, phenoxycarbonyl, benzyloxycarbonyl, $C_1$–$C_{10}$alkoxycarbonyl or $L_2$—NH—$C_1$–$C_{10}$alkyl;

$R_9$ is hydrogen, $C_1$–$C_{10}$alkyl-C(Q)—, benzyl, phenyl-C(Q)—, phenoxycarbonyl, $C_1$–$C_4$alkoxycarbonyl, $R_{18}$($R_{19}$)N—C(Q)— or $R_3$($R_4$)N—C(O)—$C_1$–$C_{10}$-alkyl; or $R_8$ and $R_9$ together form a ring —X—Y—Z—, in which X is the groups

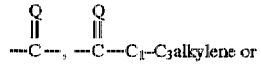

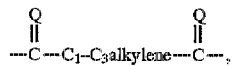

wherein
the alkylene chain can be unsubstituted or substituted by halogen, hydroxyl, $C_1$–$C_4$alkoxy or $C_1$–$C_4$alkoxycarbonyl;

Q is oxygen;

Y is oxygen, unsubstituted $C_1$— or $C_2$-alkylene or —NR$_5$—; Z is the groups

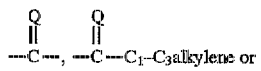

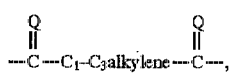

wherein the alkylene chain can be unsubstituted or substituted by halogen, hydroxyl, $C_1$–$C_4$alkoxy or $C_1$–$C_4$alkoxycarbonyl, or is

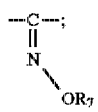

or Y and Z together are a group

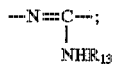

$R_5$ is hydrogen, $C_1$–$C_{10}$alkyl or unsubstituted phenoxycarbonyl, benzyloxycarbonyl, benzylcarbonyl or phenyl;

$R_7$ is hydrogen, $C_3$–$C_7$cycloalkyl, $C_1$–$C_{10}$alkyl or $C_3$–$C_{10}$alkynyl;

$R_{13}$ is hydrogen or $C_1$–$C_4$alkyl;

$R_{16}$ is $C_1$–$C_5$alkyl, phenyl or benzyl;

$R_{18}$ is unsubstituted $C_1$–$C_{10}$alkyl, $C_1$–$C_{10}$alkoxycarbonyl, benzyl, benzyloxycarbonyl or $C_1$–$C_6$alkylcarbonyl; and $R_{19}$ is hydrogen.

The process according to the invention is particularly preferably carried out for compounds of the formula I in which $R_1$ is hydroxyl, $C_1$–$C_4$alkoxy, trimethylsilyloxy, unsubstituted benzyloxy, $R_{10}$—C(O)—O—, $$R_{16}O-\underset{\underset{OR_{16}}{|}}{\overset{\overset{O}{\|}}{P}}-O- \quad \text{or} \quad R_{16}O-\underset{\underset{OR_{16}}{|}}{\overset{\overset{O}{\|}}{P}}-O-$$

$R_2$ is hydroxyl, $C_1$–$C_4$alkoxy, trimethylsilyloxy, unsubstituted benzyloxy, $R_{10}$—C(O)—O— or $L_1$—O—; or $R_1$ together with $R_2$ is —OSi($R_{11}$)$R_{20}$O— or —OC($R_{12}$)$R_{21}$O—;

$R_{10}$ is $C_1$–$C_4$alkyl or unsubstituted phenyl;

$R_{11}$ and $R_{20}$ are $C_1$–$C_4$alkyl;

$R_{12}$ and $R_{21}$ are $C_1$–$C_4$alkyl;

$R_8$ is $C_1$–$C_{10}$alkyl, $C_2$–$C_{10}$alkenyl, $C_2$–$C_{10}$alkynyl, $C_1$–$C_{10}$alkyl-C(Q)— or $C_1$–$C_{10}$alkoxycarbonyl;

$R_9$ is hydrogen, $C_1$–$C_{10}$alkyl-C(Q)—, $C_1$–$C_4$alkoxycarbonyl, phenoxycarbonyl or $R_{18}(R_{19})$N—C(Q)—; or $R_8$ and $R_9$ together form a ring —X—Y—Z—, in which X is the group $$-\overset{\overset{Q}{\|}}{C}- \quad \text{or} \quad -\overset{\overset{Q}{\|}}{C}-C_1\text{-}C_3\text{alkylene},$$

wherein the alkylene chain can be unsubstituted or substituted by halogen or hydroxyl;

Y is oxygen or —NR$_5$—;

Z is the groups $$-\overset{\overset{Q}{\|}}{C}-, \quad -\overset{\overset{Q}{\|}}{C}-C_1\text{-}C_3\text{alkylene},$$

wherein the alkylene chain can be unsubstituted or substituted by halogen or hydroxyl, or is $$-\underset{\underset{OR_7}{\diagdown}}{\overset{\overset{\|}{N}}{C}}-;$$

or Y and Z together are a group $$-\underset{\underset{NHR_{13}}{|}}{N}=C-;$$

$R_5$ is hydrogen or unsubstituted $C_1$–$C_{10}$alkyl;

$R_7$ is hydrogen, $C_3$–$C_7$cycloalkyl or unsubstituted $C_1$–$C_{10}$alkyl;

$R_{16}$ is $C_1$–$C_5$alkyl or benzyl;

$R_{18}$ is unsubstituted $C_1$–$C_{10}$alkyl or $C_1$–$C_6$alkylcarbonyl; and $R_{19}$ is hydrogen.

The process according to the invention is especially preferably carried out for compounds of the formula I in which $R_1$ is hydroxyl, unsubstituted benzyloxy or $$R_{16}O-\underset{\underset{OR_{16}}{|}}{\overset{\overset{O}{\|}}{P}}-O-;$$

$R_2$ is hydroxyl or unsubstituted benzyloxy;

$R_8$ and $R_9$ together form a ring —X—Y—Z—, in which X is the group $$-\overset{\overset{Q}{\|}}{C}-;$$

Y is —NR$_5$—;

Z is the group $$-\overset{\overset{Q}{\|}}{C}- \quad \text{or} \quad -\underset{\underset{OR_7}{\diagdown}}{\overset{\overset{\|}{N}}{C}}-;$$

$R_5$ is hydrogen or unsubstituted $C_1$–$C_4$alkyl; and $R_7$ is hydrogen or unsubstituted $C_1$–$C_{10}$alkyl.

The process according to the invention is likewise preferably carried out for compounds of the formula I, in which A is the group $$-\underset{\underset{R_1}{|}}{\overset{\overset{H}{|}}{C}}-\underset{\underset{R_2}{|}}{\overset{\overset{H}{|}}{C}}-;$$

$R_1$ is hydroxyl, $C_1$–$C_4$alkoxy, trimethylsilyloxy, unsubstituted benzyloxy, $R_{10}$—C(O)—O—, $$R_{16}O-\underset{\underset{OR_{16}}{|}}{\overset{\overset{O}{\|}}{P}}-O-, \quad R_{16}-\underset{\underset{OR_{16}}{|}}{\overset{\overset{O}{\|}}{P}}-O- \quad \text{or} \quad L_1-O-;$$

$R_2$ is hydroxyl, $C_1$–$C_4$alkoxy, trimethylsilyloxy, unsubstituted benzyloxy, $R_{10}$—C(O)—O— or $L_1$—O—; or $R_1$ together with $R_2$ is —OSi($R_{11}$)$R_{20}$O— or —OC($R_{12}$)$R_{21}$O—;

$R_{10}$ is $C_1$–$C_4$alkyl or unsubstituted phenyl;

$R_{11}$ and $R_{21}$ are $C_1$–$C_4$alkyl;

$R_{12}$ and $R_{21}$ are $C_1$–$C_4$alkyl;

$R_8$ and $R_9$ together for a ring —X—Y—Z—,
in which
X is the group

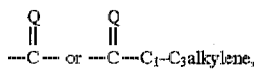

wherein
the alkylene chain can be unsubstituted or substituted by halogen or hydroxyl;
Q is oxygen;
Y is oxygen or —$NR_5$—;
Z is the groups

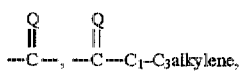

wherein
the alkylene chain can be unsubstituted or substituted by halogen or hydroxyl, or is

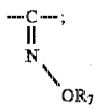

Y and Z together are a group

$R_5$ is hydrogen or unsubstituted $C_1$–$C_{10}$alkyl;
$R_7$ is hydrogen, $C_3$–$C_7$cycloalkyl or unsubstituted $C_1$–$C_{10}$alkyl;
$R_{13}$ is hydrogen or unsubstituted $C_1$–$C_{10}$alkyl or $C_1$–$C_{10}$alkylcarbonyl; and
$R_6$ is $C_1$–$C_5$alkyl or benzyl.

In particular, of these, the process which is particularly preferred is that
in which
$R_1$ and $R_2$ are hydroxyl;
$R_8$ and $R_9$ together form a ring —X—Y—Z—,
wherein
X and Z are the group

Y is —$NR_5$—;
Q is oxygen; and
$R_5$ is hydrogen.

The process according to the invention is likewise preferably carried out for compounds of the formula I
in which A is the group

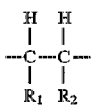

or —CH═CH—;
$R_2$ is hydroxyl, $C_1$–$C_4$alkoxy-$C_1$–$C_4$alkoxy, unsubstituted benzyloxy, $R_{10}$—C(O)—O—, $R_3(R_4)$N—,

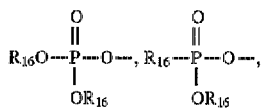

azido or $L_1$—O—;
$R_2$ is hydrogen, halogen, $R_3(R_4)$N—, azido or cyano;
$R_3$ is hydrogen, unsubstituted or substituted $C_1$–$C_{10}$alkyl, $C_1$–$C_{10}$alkylcarbonyl which is unsubstituted or substituted by hydroxyl, cyano or $C_1$–$C_4$alkylaminocarbonyl, $C_1$–$C_{C10}$alkoxycarbonyl or unsubstituted benzyloxycarbonyl;
$R_4$ is hydrogen, unsubstituted or substituted $_1$–$C_{C10}$alkyl, $C_1$–$C_{C10}$alkylcarbonyl which is unsubstituted or substituted by hydroxyl, cyano or $C_1$–$C_{C4}$alkylaminocarbonyl, $C_1$–$C_{C10}$alkoxycarbonyl or unsubstituted benzyloxycarbonyl;
$R_{10}$ is $C_1$–$C_{C4}$alkyl or unsubstituted benzyl or phenyl;
$R_8$ is unsubstituted or substituted $C_1$–$C_{C10}$alkyl, $C_2$–$C_{10}$alkenyl, $C_2$–$C_{10}$alkynyl, $C_1$–$C_{C10}$alkyl-C(Q)— or benzyloxycarbonyl, cyano, carboxyl, nitro, $C_1$–$C_{C10}$alkoxycarbonyl, $R_3(R_4)$N—C(O)— or $L_2$—NH—$C_1$–$C_{10}$alkyl;
$R_9$ is hydrogen, unsubstituted or substituted $C_1$–$C_{10}$alkyl, $C_2$–$C_{10}$alkenyl, $C_2$–$C_{10}$alkynyl, $C_1$–$C_{C10}$alkyl-C(Q)—, phenoxycarbonyl, benzyloxycarbonyl, phenoxycarbonyl-$C_1$–$C_{C10}$alkyl or benzyloxycarbonyl-$C_1$–$C_{10}$alkyl, $C_1$–$C_4$alkoxycarbonyl, $C_1$–$C_4$alkoxy-C(O)—NH—$SO_2$—, $NH_2$—$SO_2$—, $R_{18}(R_{19})$N—C(Q)— or $R_3(R_4)$N—C(O)—$C_1$–$C_{C10}$-alkyl; or
$R_8$ and $R_9$ together form a ring —X—Y—Z—,
in which
X is the groups

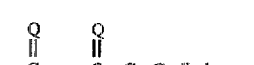

wherein
the alkylene chain can be unsubstituted or substituted by hydroxyl, amino, $C_1$–$C_{C4}$alkylamino, cyano, carboxyl, $C_1$–$C_4$alkoxycarbonyl, carbamoyl or $C_1$–$C_{C4}$alkylaminocarbonyl;
Q is oxygen;
Y is oxygen or —$NR_5$—;
Z is the groups

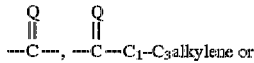

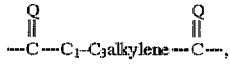

wherein
the alkylene chain can be unsubstituted or substituted by hydroxyl, amino, $C_1$–$C_{C4}$alkylamino, cyano, carboxyl, $C_1$–$C_{C4}$alkoxycarbonyl, carbamoyl or $C_1$–$C_4$alkylaminocarbonyl; or Y and Z together are a group

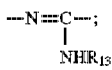

$R_5$ is hydrogen, unsubstituted $C_1$-$C_{10}$alkylcarbonyl, $C_1$-$C_{10}$alkoxycarbonyl, phenoxycarbonyl, benzylcarbonyl, benzyloxycarbonyl or phenyl;

$R_6$ is carboxyl or $C_1$-$C_4$alkoxycarbonyl;

$R_7$ is hydrogen, unsubstituted or substituted $C_1$-$C_{10}$alkyl or benzyl;

$R_{13}$ is hydrogen or unsubstituted or substituted $C_1$-$C_{10}$alkyl, $C_1$-$C_{10}$alkylcarbonyl, phenyl or benzyl;

$R_{16}$ is $C_1$-$C_5$alkyl, $C_3$-$C_5$alkenyl, phenyl or benzyl;

$R_{18}$ is $C_1$-$C_{10}$alkoxycarbonyl, phenoxycarbonyl, benzyl, benzyloxycarbonyl or $C_1$-$C_6$alkylcarbonyl; and $R_{19}$ is hydrogen, unsubstituted $C_1$-$C_{10}$alkylcarbonyl, $C_1$-$C_{10}$alkoxycarbonyl, phenoxycarbonyl, benzyl, benzyloxycarbonyl or $C_1$-$C_4$alkylaminocarbonyl.

Of these, the process which is particularly preferred is that for compounds of the formula I in which A is the group

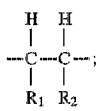

$R_1$ is hydroxyl, $R_3(R_4)N-$,

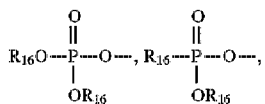

azido or $L_1-O-$;

$R_2$ is hydrogen or halogen;

$R_3$ is hydrogen, unsubstituted or substituted $C_1$-$C_{10}$alkyl, unsubstituted $C_1$-$C_{10}$-alkylcarbonyl, $C_1$-$C_{10}$alkoxycarbonyl or benzyloxycarbonyl;

$R_4$ is hydrogen, unsubstituted or substituted $C_1$-$C_{10}$alkyl, unsubstituted $C_1$-$C_{10}$alkylcarbonyl, $C_1$-$C_{10}$alkoxycarbonyl or benzyloxycarbonyl;

$R_{10}$ is $C_1$-$C_4$alkyl or unsubstituted benzyl or phenyl;

$R_8$ is unsubstituted or substituted $C_1$-$C_{10}$alkyl, $C_2$-$C_{10}$alkynyl or $C_1$-$C_{10}$alkyl-C(Q)—, cyano, $C_1$-$C_{10}$alkoxycarbonyl or $L_2$—NH—$C_1$-$C_{10}$alkyl;

$R_9$ is hydrogen, unsubstituted or substituted $C_1$-$C_{10}$alkyl, $C_1$-$C_{10}$alkyl-C(Q)—, $NH_2$—$SO_2$— or $R_{18}(R_{19})N$—C(Q)—; or $R_8$ and $R_9$ together form a ring —X—Y—Z—, in which X is the groups

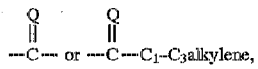

wherein the alkylene chain can be unsubstituted or substituted by hydroxyl or amino;

Q is oxygen;

Y is oxygen or —$NR_5$—;

Z is the groups

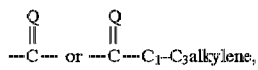

wherein the alkylene chain can be unsubstituted or substituted by hydroxyl, amino, $C_1$-$C_4$alkylamino, $C_1$-$C_4$alkoxycarbonyl or $C_1$-$C_4$alkylaminocarbonyl;

$R_5$ is hydrogen, unsubstituted $C_1$-$C_{10}$alkylcarbonyl, $C_1$-$C_{10}$alkoxycarbonyl, benzyloxycarbonyl or phenyl;

$R_6$ is $C_1$-$C_4$alkoxycarbonyl;

$R_7$ is hydrogen, unsubstituted or substituted $C_1$-$C_{10}$alkyl or benzyl;

$R_{13}$ is hydrogen or unsubstituted or substituted $C_1$-$C_{10}$alkyl, $C_1$-$C_{10}$alkylcarbonyl, phenyl or benzyl;

$R_{16}$ is $C_1$-$C_5$alkyl, $C_3$-$C_5$alkenyl, phenyl or benzyl;

$R_{18}$ benzyl or benzyloxycarbonyl; and $R_{19}$ is hydrogen, unsubstituted $C_1$-$C_{10}$alkylcarbonyl or benzyl.

The process according to the invention for the preparation of compounds of the formula I follows equation 1.

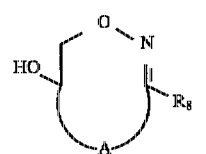

VI

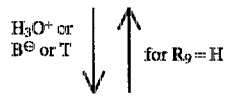

for $R_9$=H

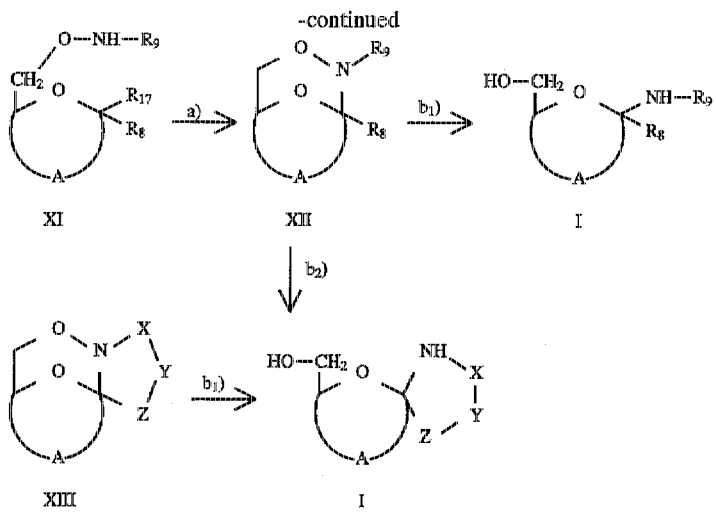

b$_1$) R$_8$ and R$_9$ are as defined, with the exception of R$_8$ and R$_9$ together forming a ring —X—Y—Z—;

b$_2$) R$_8$ and R$_9$ are as defined, with the exception of C$_1$–C$_{10}$alkyl, C$_2$–C$_{10}$alkenyl, C$_2$–C$_{10}$alkynyl, phenyl or benzyl.

The starting compounds of the formula XI can be prepared by a process analogous to known processes, such as are described, for example, in J. Org. Chem. 41, 1836 (1976), Tetrahedron 47, 2145 (1991), J. Chem. Soc. 1958, 1632, J. Org. Chem. 23, 1257 (1958), Synthesis 1976, 682, Tetrahedron Lett. 25, 395 (1984), Synthesis 1990, 1031, Synthesis 1991, 933 and Helv. Chim. Acta 65, 1404 (1982). In these processes, the free hydroxyl group is in general substituted by N-hydroxyphthalimides and then converted into the corresponding alkoxyamines with hydrazine.

The cyclization of the compound of the formula XI (reaction step a)), in which A, R$_8$, R$_9$ and R$_{17}$ are as defined, can preferably be carried out in an aprotic solvent in the presence of 1. Lewis acids, for example BF$_3$.O(C$_2$H$_5$)$_2$, tritylium perchlorate ((C$_6$H$_5$)$_3$C(ClO$_4$)), F—Si(CH$_3$)$_3$, Cl—Si(CH$_3$)$_3$, Br—Si(CH$_3$)$_3$, CN—Si(CH$_3$)$_3$, CF$_3$SO$_2$OSi(CH$_3$)$_3$ (=trimethylsilyl triflate, TMSOTf), FSO$_2$OSi(CH$_3$)$_3$, SnCl$_4$, AgCl$_4$, (CH$_3$)$_3$SiClO$_4$, C$_4$F$_9$SO$_2$OSi(CH$_3$)$_3$, C$_4$HF$_8$SO$_2$OSi(CH$_3$)$_3$, SO$_2$[Si(CH$_3$)$_3$]$_2$, Hg(CN)$_2$, HgCl$_2$, HgBr$_2$, Hg(OAc)$_2$, TiCl$_4$ or (CH$_3$)$_2$S(SCH$_3$)BF$_4$, or 2. Brönsted acids, for example C$_1$–C$_6$alkyl-SO$_3$H, phenylsulfonic acid which is unsubstituted or substituted by C$_1$–C$_4$alkyl, C$_1$–C$_4$haloalkyl, halogen, cyano or nitro, camphorsulfonic acid, sulfamic acid (H$_2$N—SO$_3$H), CF$_3$COOH, CF$_3$SO$_3$H or Cl$_2$CHCOOH, or 3. without catalysis, at temperatures of –78° C. to +120° C.

Aprotic organic solvents are, for example, aromatic hydrocarbons, for example benzene, toluene or xylenes, chlorinated hydrocarbons, for example methylene chloride, chloroform, carbon tetrachloride or 1,2-dichloroethane, esters, for example ethyl acetate or propyl acetate, aliphatic or cyclic ethers, for example diethyl ether, tetrahydrofuran, dioxane or 1,2-dimethoxyethane (DME), amides, for example N,N-dimethylformamide, dialkyl sulfoxides, for example dimethyl sulfoxide (DMSO), nitriles, for example acetonitrile, or nitroalkanes, for example nitromethane. Advantageously, in this step, the compound of the formula XI is dissolved in the aprotic solvent, and the Lewis or Brönsted acid is added in amounts of 0.1 to 1.0 mol. The reaction mixture is then preferably stirred at temperatures of –40° C. up to the reflux temperature of the reaction mixture for 15 minutes up to 72 hours. The reaction is as a rule ended within a relatively short time or after a few hours, depending on the solvent used, the catalyst and the reaction temperature.

When the cyclization has ended, after deactivation of the catalyst, preferably with an amine, for example triethylamine, the product can be isolated and purified in a manner known per se.

In a preferred cyclization reaction, the compound of the formula XI is first dissolved in an aprotic organic solvent, for example acetonitrile or nitromethane, a catalytic amount (0.1 mol) of Lewis acid, for example trimethylsilyl trifluoromethanesulfonate ((TMSOTf, CF$_3$SO$_2$OSi(CH$_3$)$_3$), or Brönsted acid, for example sulfamic acid (NH$_2$—SO$_3$H), is added and the mixture is then stirred at temperatures of 0° C. to 25° C. until conversion is complete (monitoring by means of analytical thin layer chromatography).

If appropriate, the group —CH$_2$—O—NH—R$_9$ in the compound of the formula XI can be silylated beforehand by standard methods, such as are described, for example, in Z. Chem. 4, 303 (1964) and J. Org. Chem. 39 (25), 3657 (1974), for example with hexamethyldisilazane (HMDS), (CH$_3$)$_3$SiCl or CF$_3$SO$_2$OSi(CH$_3$)$_3$ in the presence of a base, for example tri-C$_1$–C$_4$alkylamine, pyridine or in the presence of hydrides, for example NaH.

If R$_9$ is hydrogen, the bicyclic compound of the formula XII is slowly converted into the thermodynamically more stable monocyclic compound of the formula VI when left to stand. The bicyclic compound of the formula XII is formed again in the presence of catalytic amounts of acid (H$_3$O$^\oplus$), for example dilute hydrochloric acid, or base (B$^\ominus$), for example dilute sodium hydroxide solution, or by gentle heating (T). (cf. also Example H3).

Under the reaction conditions chosen according to reaction path b$_1$) or b$_2$)—b$_1$), the compound of the formula VI is converted completely, i.e. without isomerization, into the compound of the formula XII, which then further reacts by itself into the compound of the formula I or XIII and I.

Process variant b$_1$) can advantageously be carried out by a process analogous to known processes, such as are described, for example, in Chem. Ber. 101, 2559 (1968), Tetrahedron 41, 3455 (1985), Tetrahedron Lett. 27, 3119

(1986), Tetrahedron Lett. 1978, 4763 and Tetrahedron Lett. 31, 3351 (1990), by splitting the N—O bond either by hydrogenolysis, for example with $H_2$—Pd/C, $H_2$—Pt/C, $H_2$—Ra/Ni, Zn/AcOH, $Na/NH_3$, $Li/NH_3$ or Al—Hg, or with an organometallic compound, for example a metal carbonyl, such as $Mo(CO)_6$.

Organometallic compounds are more suitable for cleavage of the N—O bond in the case of a substituent $R_9$ which has a deactivating effect on the N—O bond, for example a carbamoyl group.

This process variant $b_1$) leads to 1',1'-disubstituted nucleosides of the formula I.

In process variant $b_2$)—$b_1$), an intramolecular cyclization reaction takes place analogously to known processes, for example aldol, acyloin or Mitsunobu condensation, halocyclization, peptide coupling or nucleophilic addition, before cleavage of the N—O bond.

For example, according to route $b_2$), the tricyclic compounds of the formula XIII can be prepared from the bicyclic compounds of the formula XII, depending on the substituents $R_8$ and $R_9$, analogously to the following standard cyclization methods:

1) J. Org. Chem. 39, 2644 (1974) with tetrabutylammonium fluoride ($Bu_4N^\oplus F^\ominus$) from compounds of the formula XII

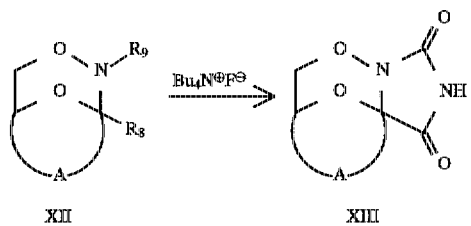

in which $R_9$ is $C_1$–$C_4$alkoxycarbonyl or benzyloxycarbonyl;
$R_8$ is $R_3(R_4)N$—C(O)—;
$R_3$ and $R_4$ are hydrogen;
A is the group

and $R_1$ together with $R_2$ is —$OC(R_{12})R_{21}O$—;

2) Synthesis 1981, 1 with an intramolecular dehydration (Mitsunobu condensation) with diethyl azodicarboxylate (DEAD)/triphenylphosphine from compounds of the formula XII,

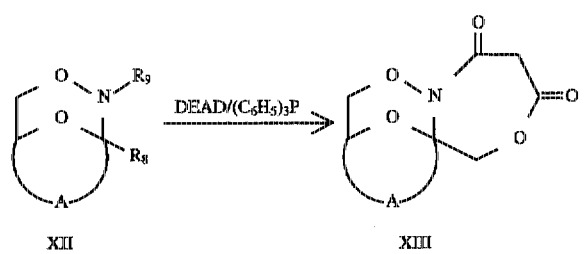

in which $R_9$ is carboxyl-substituted $C_1$alkyl-C(O)—;
$R_8$ is hydroxyl-substituted $C_1$alkyl;
A is the group

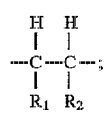

and $R_1$ together with $R_2$ is —$OC(R_{12})R_{21}O$—;

3) Synthesis 1977, 413 with the peptide coupling reagent benzotriazolyl-oxytris[dimethylamino]phosphonium hexafluorophosphate (BOP) from compounds of the formula XII

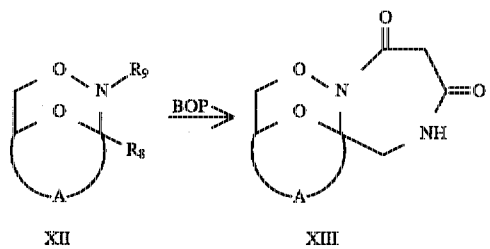

in which $R_9$ is carboxyl-substituted $C_1$alkyl-C(O)—;
$R_8$ is amino-substituted $C_1$alkyl;
A is the group

and $R_1$ together with $R_2$ is —$OC(R_{12})R_{21}O$—; and

4) Tetrahedron Lett. 30, 2045 (1989) with a halocyclization with N-bromosuccinimide (NBS) from compounds of the formula XII,

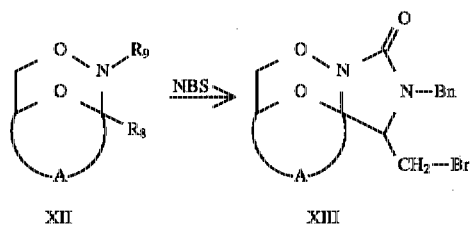

in which $R_9$ is $R_{18}(R_{19})N$—C(O)—;
$R_{18}$ is benzyl (Bn);
$R_{19}$ is hydrogen;
$R_8$ is $C_2$alkenyl;

A is the group

and

R$_1$ is together with R$_2$ is —OC(R$_{12}$)R$_{21}$O—.

This process variant b$_2$)—b$_1$) leads to 1'-spiro-nucleosides of the formula I after cleavage of the N—O bond.

The present process according to the invention has the following advantages over the prior art:

1. high ability to form derivatives in respect of both the sugar and the base moiety for the preparation of a large number of 1',1'-disubstituted and 1'-spiro-nucleotides;
2. high ability to form derivatives with respect to the choice of the substituents R$_8$ and R$_9$, and associated with this, wide possibilities of variation for the modified intramolecular Vorbrüggen coupling (cyclization conditions);
3. the intermediates of the formulae XII and XII cannot be epimerized;
4. the stereospecificity of the glycosylation reaction on the anomeric 1'-carbon atom (reaction step a)) is independent of the group A or the nature of the substituents R$_1$ and R$_2$ in the 3'- and 2'-position of the compound of the formula XI if A is the group

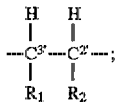

5. the stereospecificity of the glycosylation reaction on the anomeric 1'-carbon atom (reaction step a)) is independent of the stereochemistry of the substituents R$_1$ and R$_2$ in the 3'- and 2'-position of the compound of the formula XI if A is the group

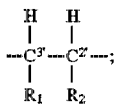

6. silylation of the cyclizing group —CH$_2$—O—NH—R$_9$ before the cyclization reaction is not necessary;
7. the cleavage of the N—O bond in reaction step b$_1$) is carried out under mild reaction conditions and is compatible for a large number of functional (protective) groups; and
8. easy formation of derivatives of the —C(Q)— group bonded to the angular ring carbon atom in the compound of the formula XIII if X and Z are a group —C(Q)— and Y is —NR$_5$—.

The reason for this lies in the different reactivity of this —C(Q)— group compared with a usual hydantoin —C(Q)— group (probably because of the

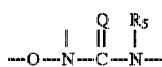

bridge in the compound of the formula XIII). This finding allows additional derivatization possibilities of the intermediates of the formula XIII and therefore also of the nucleosides of the formula I (exemplified with the aid of Example H5).

The compounds of the formulae XII and XIII are novel. They are valuable intermediates for the synthesis of the compounds of the formula I. The invention thus also relates to these novel compounds and to processes for their preparation, as well as to the use of the compounds of the formulae XII and XIII for the preparation of compounds of the formula I.

For the intermediates of the formulae XII and XIII, A, R$_8$, R$_9$, X, Y and Z are as defined as preferred for the compounds of the formula I.

The process for the preparation of compounds of the formula XII

in which the radicals A, R$_8$ and R$_9$ are as defined in claim 1, comprises cyclizing a compound of the formula XI

in which

A, R$_8$, R$_9$ and R$_{17}$ are as defined in claim 1, in an aprotic solvent in the presence of a Lewis or Brönsted acid at temperatures of −78° C. to +120° C.

The compounds of the formula XI are preferably cyclized in nitromethane or acetonitrile in the presence of a catalytic amount of CF$_3$SO$_2$OSi(CH$_3$)$_3$, p-toluenesulfonic acid or NH$_2$—SO$_3$H at temperatures of 0° C. his 25° C.

The process for the preparation of compounds of the formula XIII

in which

A, X, Y and Z are as defined in claim 1, comprises cyclizing a compound of the formula XI

in which

A and R$_{17}$ are as defined in claim 1 and R$_8$ and R$_9$ are as defined in claim 1, with the exception of C$_1$–C$_{10}$alkyl, C$_2$–C$_{10}$alkenyl, C$_2$–C$_{10}$alkynyl, phenyl and benzyl, to give the compound of the formula XII

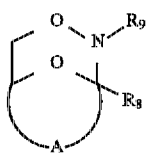 (XII)

and $b_2$) subsequently cyclizing this compound again in a manner known per se to give the compound of the formula XIII. Reactions are, for example, aldol, acyloin or Mitsunobu condensation, halocyclization, peptide coupling or nucleophilic addition, such as are described, for example, in J. Org. Chem. 39, 2644 (1974), Synthesis 1981, 1, Synthesis 1977, 413 and Tetrahedron Lett. 30, 2045 (1989).

The present process according to the invention can be used, in particular, for the preparation of the microbial metabolite (+)-hydantocidin.

(+)-Hydantocidin of the formula Ia

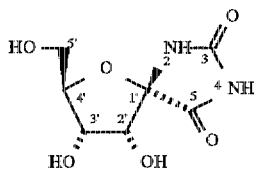 (Ia)

is a naturally occurring herbicidal spiro-nucleoside which has a regulatory action on plant gowth, has been isolated from the fermentation culture of *Streptomyces hygroscopicus* (SANK 63584 and TU-2474) and has been described in EP-A-0 232 572 and DE-A -4 129 616.

(+)-Hydantocidin is the first nucleoside having a spiro-hydantoin ring on the anomeric 1'-carbon atom of a sugar, i.e. D-ribofuranose. It is one of 16 possible stereoisomers. Structure/activity relationships according to Tetrahedron 47, 2121 and 2145 (1991) have shown that only (+)-hydantocidin with the N-β-anomeric structure is biologically active.

Because of its unusual structure, the low fermentative yield and the potential biological activity, for example as a herbicide and plant growth regulator, a great interest has rapidly arisen in this compound, and several syntheses for the preparation of (+)-hydantocidin are therefore known, for example in Tetrahedron 47, 2111 and 2133 (1991), Tetrahedron Lett. 34 (39), 6289 (1993), Tetrahedron Lett. 34 (46), 7391 (1993), JP-A-02 085 287, JP-A-02 167 283 and DE-B-4 129 728.

However, none of these syntheses is satisfactory in respect of the purity and yield of the end product, accessibility of the starting compounds, reaction procedure and stereospecificity. In particular, the problem of the configuration around the anomeric 1'-carbon atom of (+)-hydantocidin (N-β-anomer) cannot be solved satisfactorily by synthesis by the known processes.

A particular object of the present invention is thus to propose a process for the preparation of (+)-hydantocidin which is largely free from such disadvantages.

According to the invention, this object is achieved by using as the key step a modified intramolecular Vorbrüggen coupling (reaction step a) in equations 1 and 2 and reaction step (4) in equations 3 and 4 to form an oxygen-nitrogen bridge between the 5'-$CH_2$ group and the anomeric 1'-carbon atom, glycosylation) which exclusively gives the N-β-isomer of the formula XIIa below. The configuration of the glycosylated carbon atom in the 1'-position is determined here by the configuration of the carbon atom in the 4'-position of the compound of the formula XIa below by formation of the bicyclic isoxazolidine of the formula XIIa.

The invention thus furthermore relates to a process for the preparation of (+)-hydantocidin of the formula Ia

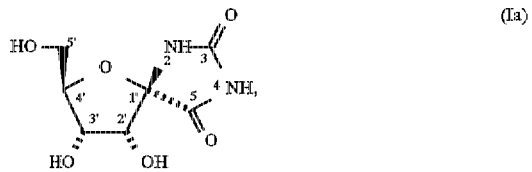 (Ia)

which comprises a) cyclizing the compound of the formula XIa

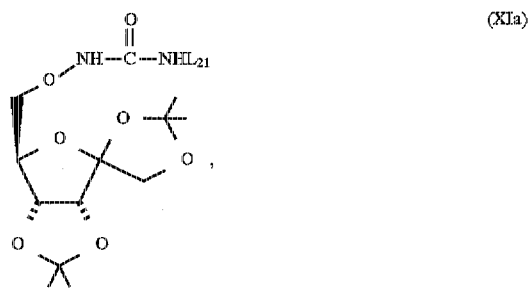 (XIa)

in which $L_{21}$ is hydrogen, benzyl, acetyl, tosyl, 2-nitrobenzyl, 3,4-dimethoxybenzyl and, in particular, p-methoxybenzyl, with a catalytic amount of a Lewis or Brönsted acid in an aprotic organic solvent to give the compound of the formula XIIa

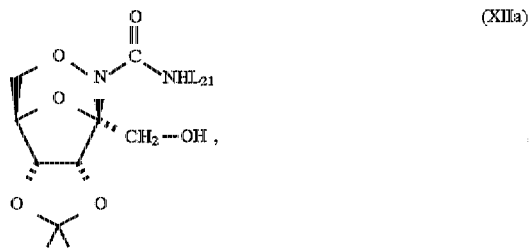 (XIIa)

in which $L_{21}$ is as defined, and $b_2$) subjecting this compound to further cyclization by reaction with an oxidizing agent and, in the tricyclic compound of the formula VIIIa thus obtained

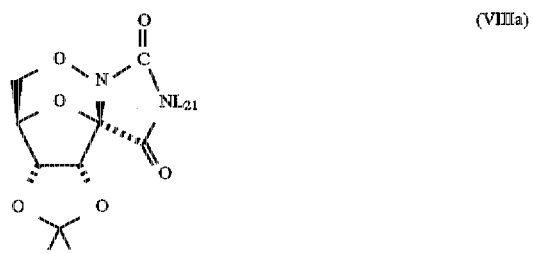 (VIIIa)

splitting off the radical $L_{21}$ by oxidation or reduction, in the compound of the formula XIIIa thus obtained

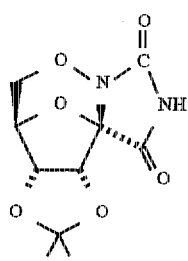
(XIIIa)

splitting the N—O bond with an organometallic compound or by hydrogenolysis to give the compound of the formula XIVa

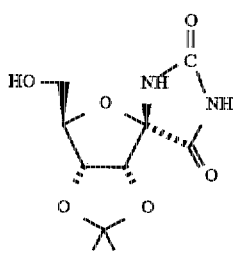
(XIVa)

and subsequently hydrolysing this to remove the isopropylidene protective group.

The abovementioned process according to the invention for the preparation of (+)-hydantocidin of the formula Ia follows equation 2.

Equation 2:

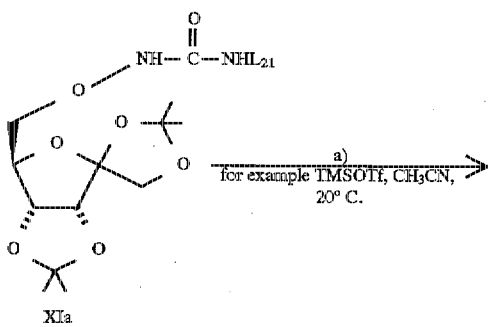

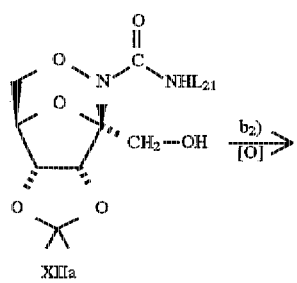

Equation 2:

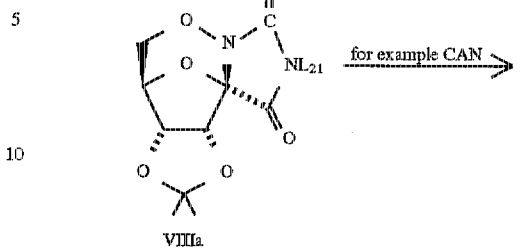

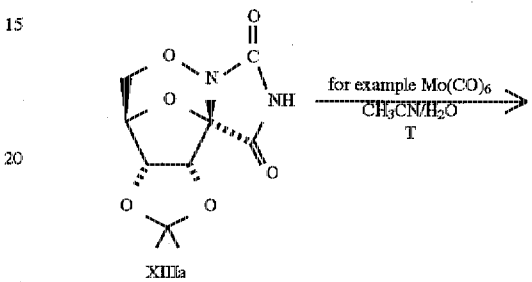

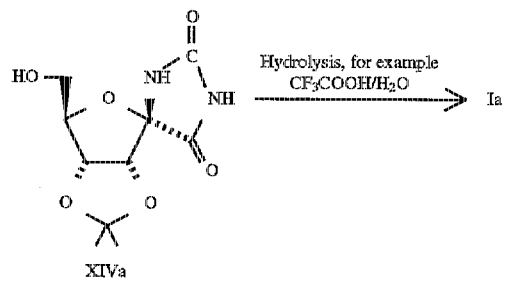

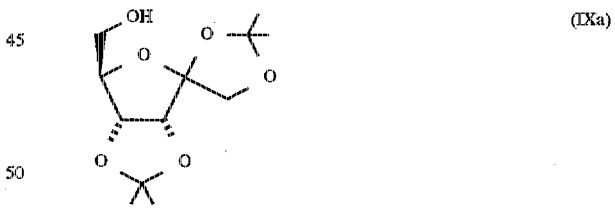

The synthesis according to equation 2 starts from the urea derivative of the formula XIa, in which $L_{21}$ is as defined, but in particular is the p-methoxybenzyl radical. The compound of the formula XIa is easily obtainable, for example, from 1',2:3',4'-di-O-isopropylidene-D-psicofuranose of the formula IXa

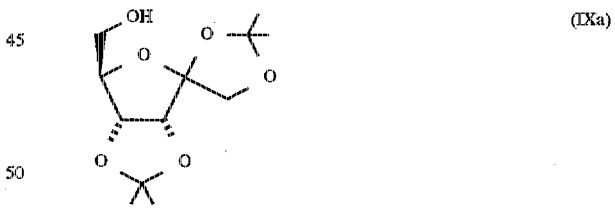

(IXa)

via 3 reaction steps analogously to those shown in equation 3.

a) By reaction with a catalytic amount of Lewis or Brönsted acid, for example trimethylsilyl trifluoromethanesulfonate ($CF_3SO_2OSi(CH_3)_3$, trimethylsilyl triflate, TMSOTf), $BF_3 \cdot O(C_2H_5)_2$, $SnCl_4$, $TiCl_4$ or $(C_6H_5)_3C(ClO_4)$, or sulfamic acid ($NH_2$—$SO_3H$) or p-toluenesulfonic acid, in an aprotic organic solvent, for example acetonitrile or nitromethane, preferably at temperatures of 0° C. to 25° C., the bicyclic isoxazolidine of the formula XIIa is obtained in which the configuration on the anomeric carbon atom (1'-position) is fixed and thus can no longer be epimerized.

The advantages of the present process step according to the invention over the prior art are:

1. the simplicity of the glycosylation reaction;
2. the stereospecificity of the glycosylation reaction on the anomeric carbon atom in the 1'-position, which is independent of the nature and stereochemistry of the substituents in the 2'- and 3'-position of the compound of the formula XIa;
3. epimerization of the intermediates of the formulae XIIa and XIIIa is excluded; and
4. silylation of the cyclizing —CH$_2$—O—NH—C(O)—NHL$_{21}$ group in the compound of the formula XIa before the cyclization reaction is not necessary.

b$_2$) The reaction of the intermediate carbinol of the formula XIIa with an oxidizing agent, for example Jones reagent, is carried out analogously to that described, for example, in J. Org. Chem. 40, 3376 (1975) and leads to the tricyclic isoxazolidine-hydantocidin of the formula VIIIa, which, after hydrogenolysis, for example with Na/NH$_3$, or oxidation, for example with 2,3-dichloro-5,6-dicyano-1,4-benzoquinone (DDQ), boron tribromide (BBr$_3$), trimethylsilyl iodide (TMSI) or, preferably, with cerium ammonium nitrate (CAN), analogous to that described, for example, in Chem. Lett. 1983, 1001 and Bull. Chem. Soc. Japan 58, 1413 (1985), gives the crystalline compound of the formula XIIIa. Cleavage of the N—O bond in the compound of the formula XIIIa is effected with an organometallic compound, for example a metal carbonyl, such as Mo(CO)$_6$, in an acetonitrile/water mixture at elevated temperature, as described, for example, in Tetrahedron Lett. 31, 3351 (1990), or with H$_2$—Ra/Ni. The customary ring-opening methods, for example via hydrogenolysis with H$_2$—Pd/C, H$_2$—Pt/C, Zn/AcOH, Li/NH$_3$ or Al—Hg, analogously to Chem. Ber. 101, 2559 (1968); Tetrahedron 41, 3455 (1985); Tetrahedron Lett. 27, 3119 (1986); and Tetrahedron Lett. 1978, 4763), do not lead to the goal in the present case, probably because of deactivation of the N—O bond by the carbamoyl group. Subsequent hydrolytic removal of the isopropylidene protective group, for example with aqueous formic acid, acetic acid or hydrochloric acid, with methanolic p-toluenesulfonic acid or, preferably, with aqueous trifluoroacetic acid by standard methods, finally gives the desired (+)-hydantocidin of the formula Ia in good yields and a good purity.

The compounds of the formulae XIIa, VIIIa and XIIIa are novel. The invention thus also relates to these novel compounds and to processes for their preparation, as well as to the use of the compounds of the formulae XIIa, VIIIa and XIIIa for the preparation of (+)-hydantocidin of the formula Ia.

The invention also relates to a process for the preparation of (+)-hydantocidin of the formula Ia

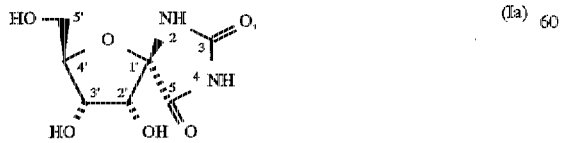
(Ia)

which comprises (1) reacting the compound of the formula IXa

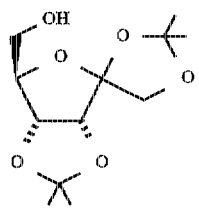
(IXa)

with an N-hydroxyimide and (2) hydrazine hydrate, (3) converting the compound of the formula Xa thus obtained

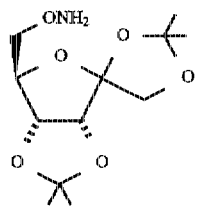
(Xa)

with an isocyanate of the formula IV $$L_{21}N=C=O \qquad (IV),$$

in which

L$_{21}$ is hydrogen, benzyl, acetyl, tosyl, 2-nitrobenzyl, 3,4-dimethoxybenzyl or p-methoxybenzyl, into the compound of the formula XIa

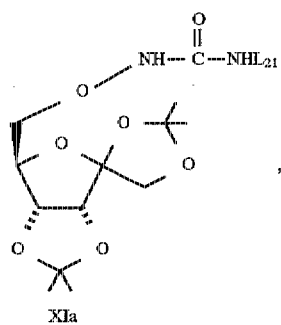
(XIa)

(4) subsequently cyclizing this with a catalytic amount of a Lewis or Brönsted acid in an aprotic organic solvent to give the compound of the formula XIIa

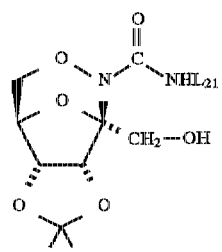
(XIIa)

(5) subjecting this compound to a further cyclization by reaction with an oxidizing agent and (6) in the tricyclic compound of the formula VIIIa thus obtained

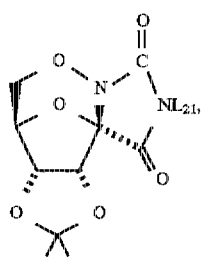
(VIIIa)

in which, in the compounds of the formulae XIa, XIIa and VIIIa the radical $L_{21}$ is as defined, splitting off the radical $L_{21}$ by oxidation or reduction and thus converting the compound into the compound of the formula XIIIa

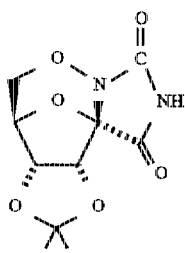
(XIIIa)

(7) in which the N—O bond is split with an organometallic compound or by hydrogenolysis to give the compound of the formula XIVa

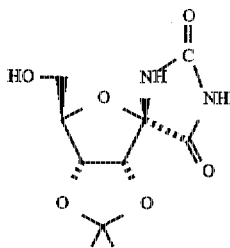
(XIVa)

and (8) subsequently hydrolysing this compound to remove the isopropylidene protective group.

The abovementioned process according to the invention for the preparation of (+)-hydantocidin of the formula Ia follows equation 3.

Equation 3:

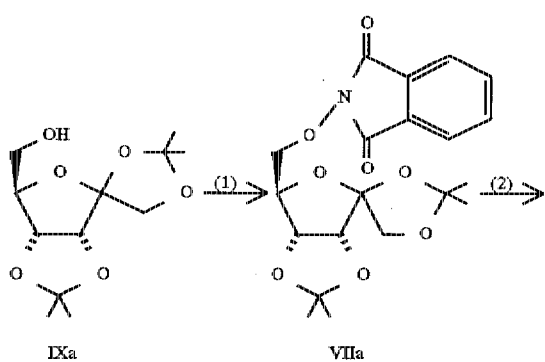

Equation 3:

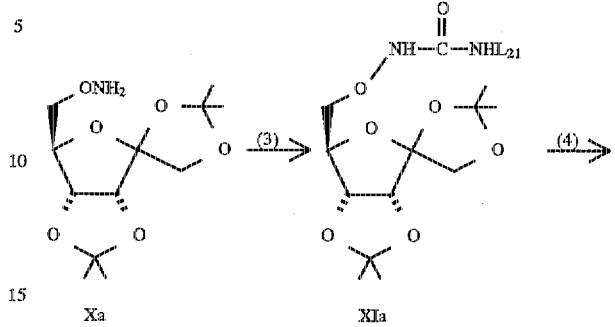

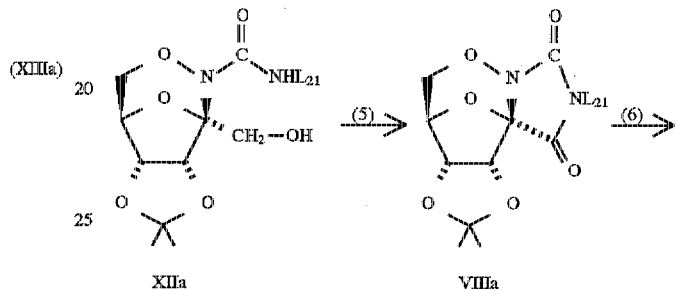

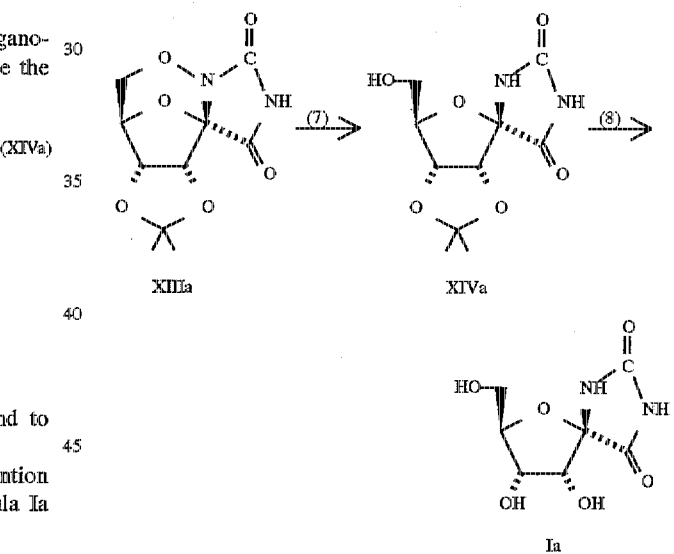

The synthesis according to equation 3 starts from the readily accessible 140 ,2:3',4'-di-O-isopropylidene-D-psicofuranose of the formula IXa, which can be obtained on a large scale (kg quantities) from D-fructose via four reaction steps, for example by the process according to Moffat (J. Org. Chem. 41, 1836 (1976) and Tetrahedron 47, 2145 (1991).

The alkoxyamine derivative of the formula Xa is prepared in a 2-stage reaction by means of substitution of the 5'-OH in the compound of the formula IXa by an N-hydroxyimide, for example N-hydroxyphthalimide (1) and subsequent hydrolysis (2) analogously, for example, to J. Chem. Soc. 1958, 1632. J. Org. Chem. 23, 1257 (1958) and Helv. Chim. Acta 46, 766 (1963), or hydrazinolysis (2) analogously to, for example, Synthesis 1976, 682 and Helv. Chim. Acta 65, 1404 (1982). The alkoxyamine derivative is converted (3) into the urea derivative of the formula XIa with an isocyanate of the formula IV L$_{21}$N=C=O (IV), for example trimethylsilyl isocyanate or p-methoxybenzyl isocyanate, prepared by introducing phosgene into a suspension of p-methoxybenzylamine hydrochloride in chlorobenzene at 115° C. and distilling off the resulting isocyanate at 83° C./0.08 mm Hg.

This urea derivative of the formula XIa at the same time is the starting substance for the (+)-hydantocidin synthesis according to equation 2.

(4) By reaction with a catalytic amount of a Lewis or Brönsted acid, for example trimethylsilyl trifluoromethanesulfonate (trimethylsilyl triflate, TMSOTf), TiCl$_4$, (C$_6$H$_5$)$_3$C (ClO$_4$), BF$_3$.O(C$_2$H$_5$)$_2$, SnCl$_4$, p-toluenesulfonic acid (p-Ts) or NH$_2$—SO$_3$H, in an aprotic organic solvent, for example acetonitrile or nitromethane, preferably at temperatures of 0° C. to 25° C., the bicyclic isoxazolidine of the formula XIIa is obtained in which the configuration on the anomeric carbon atom is fixed in the 1'-position and thus can no longer be epimerized.

The advantages of the present process step according to the invention over the prior art are:
1. the easy accessibility of the starting compound of the formula IXa;
2. the simplicity of the glycosylation reaction;
3. the stereospecificity of the glycosylation reaction on the anomeric carbon atom in the 1'-position, which is independent of the nature and stereochemistry of the substituents in the 2'- and 3'-position of the compound of the formula XIa;
4. epimerization of the intermediates of the formula XIIa (and XIIIa) is excluded; and
5. silylation of the cyclizing —CH$_2$—O—NH—C(O)—NHL$_{21}$ group before the cyclization reaction is not necessary.

The reaction of the intermediate carbinol of the formula XIIa with an oxidizing agent, for example Jones reagent, (5) is carried out analogously to that described, for example, in J. Org. Chem. 40, 3376 (1975) and leads to tricyclic isoxazolidine-hydantocidin of the formula VIIIa, which (6) gives the crystalline compound of the formula XIIIa by hydrogenolysis, for example with Na/NH$_3$, or oxidation, for example with 2,3-dichloro-5,6-dicyano-1,4-benzoquinone (DDQ), boron tribromide (BBr$_3$), trimethylsilyl iodide (TMSI) or cerium ammonium nitrate (CAN), analogously to that described, for example, in Chem. Lett. 1983, 1001 and Bull. Chem. Soc. Japan 58, 1413 (1985). The cleavage of the N—O bond (7) in the compound of the formula XIIIa is effected with an organometallic compound, for example a metal carbonyl, such as Mo(CO)$_6$ in an acetonitrile/water mixture at elevated temperature, as described, for example, in Tetrahedron Lett. 31, 3351 (1990), or with H$_2$—Ra/Ni. The customary ring-opening methods, for example via hydrogenolysis with H$_2$—Pd/C, H$_2$—Pt/C, Zn/AcOH, Li/NH$_3$ or Al—Hg, analogously to Chem. Ber. 101, 2559 (1968); Tetrahedron 41, 3455 (1985); Tetrahedron Lett. 27, 3119 (1986); and Tetrahedron Lett. 1978, 4763), do not lead to the goal in the present case, probably because of deactivation of the N—O bond by the carbamoyl group. The subsequent hydrolytic removal of the isopropylidene protective group, for example with aqueous trifluoroacetic acid, formic acid, acetic acid, or hydrochloric acid, or with methanolic p-toluenesulfonic acid by standard methods finally gives the desired (+)-hydantocidin of the formula Ia in good yields (36%, starting from the compound of the formula IXa) and a good purity.

The invention relates to a further process for the preparation of the compound of the formula Ia

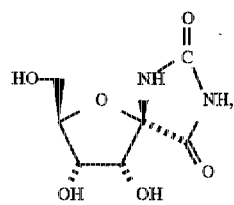
(Ia)

which comprises (9) reacting the compound of the formula IIb

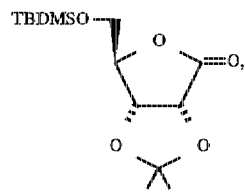
(IIb)

in which
TBDMS is the protective group

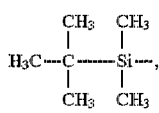, with an acetylide and subsequently with acetic anhydride, and (10) removing the TBDMS protective group, in the compound of the formula IXb thus obtained

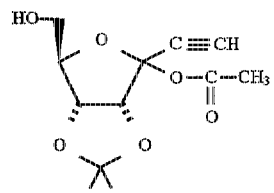
(IXb)

(11) of N-hydroxyphthalimide (12) followed by hydrazinolysis, obtaining the alkoxylamine derivate of the formula XIb

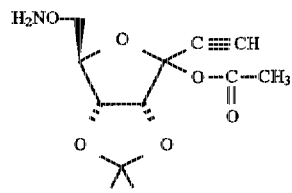
(XIb)

and (4) cyclizing this with a catalytic amount of Lewis or Brönsted acid in an aprotic organic solvent to give the compound of the formula XIIb

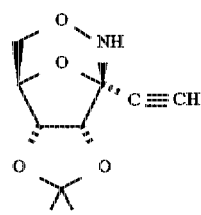
(XIIb)

and (3) converting this with p-methoxybenzyl isocyanate into the compound of the formula XIIe

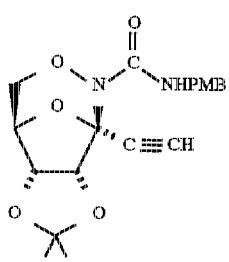

(XIIe)

and (13) subsequently reducing this to give the compound of the formula XIIf

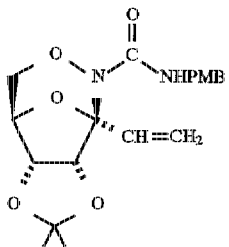

(XIIf)

subjecting the latter compound, (14) after ozonolysis and reaction with dimethyl sulfide, (15) to a further oxidation to give the compound of the formula VIIIa

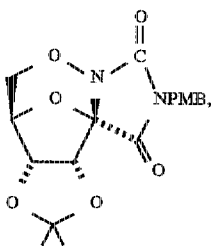

(VIIIa)

wherein in the compounds of the formulae XIIe, XIIf and VIIIa, the PMB radical is the p-methoxybenzyl group, (6) splitting off the radical PMB in the compound of the formula VIIIa with cerium ammonium nitrate and thus converting the compound into the compound of the formula XIIIa

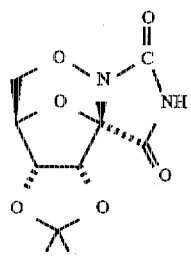

(XIIIa)

(7) in which the N—O bond is split with an organo-metallic compound or by hydrogenolysis to give the compound of the formula XIVa

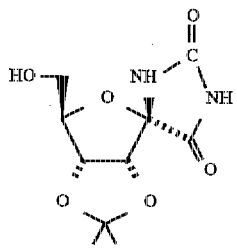

(XIVa)

(8) and subsequently hydrolysing this to remove the isopropylidene protective group.

This other example for the preparation of (+)-hydantocidin of the formula Ia on the basis of the present process according to the invention is illustrated in equation 4.

Equation 4:

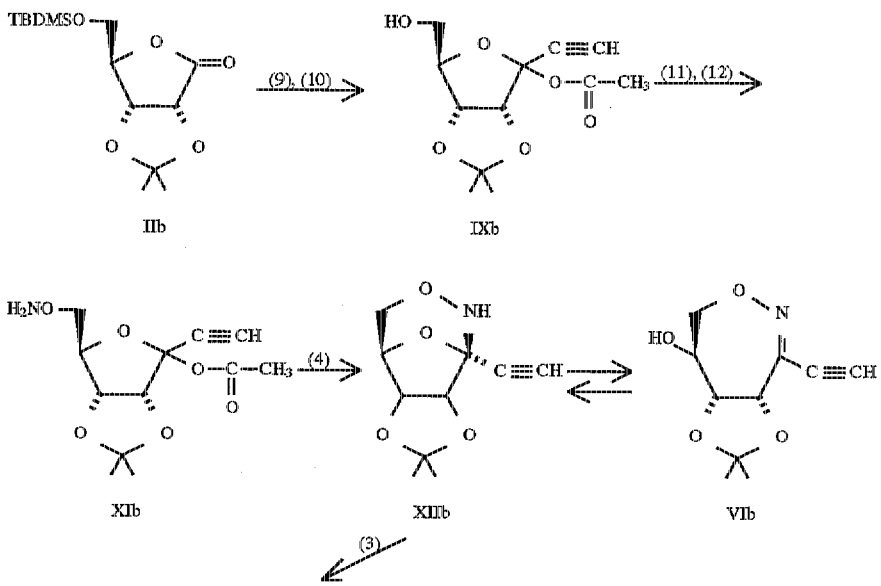

Equation 4:

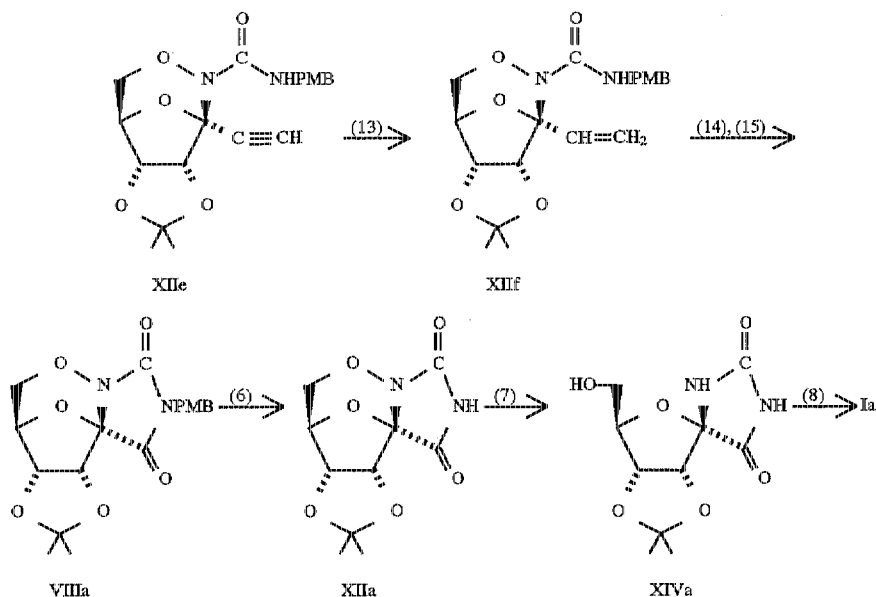

The synthesis according to equation 4 starts from protected D-ribonolactone of the formula IIb, in which TBDMS is the protective group

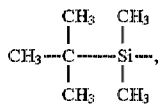

synthesis of which can be carried out in a simple manner (kg quantities), for example by the process as described in Tetrahedron Lett. 25, 395 (1984), Synthesis 1990, 1031 and Synthesis 1991, 933.

In a 2-stage reaction (9) and (10), the lactone of the formula IIb is converted into the acetylenecarbinol derivative of the formula IXb, by adding, for example analogously to J. Org. Chem. 45, 1920 (1980), a reactive lithium acetylide solution, prepared from trimethylsilyl-acetylene (TMS-acetylene) and n-butyllithium in an inert organic solvent, to the lactone of the formula IIb, (9) acetylating the resulting carbinol function with acetic anhydride and then (10) splitting off the TBDMS protective group by standard methods, for example with tetrabutylammonium fluoride. The acetylenecarbinol derivative of the formula IXb is then reacted, for example, with N-hydroxyphthalimide in the presence of triphenylphosphine and diethyl azodicarboxylate (DEAD) (11) and the alkoxyamine derivative of the formula XIb is prepared by subsequent hydrazinolysis (12), for example analogously to Synthesis 1976, 682 and Helv. Chim. Acta 65, 1404 (1982). (4) By reaction with a catalytic amount of Lewis or Brönsted acid, for example $CF_3SO_2OSi(CH_3)_3$ or $NH_2$—$SO_3H$, in an aprotic solvent, for example acetonitrile or nitromethane, preferably at temperatures of 0° C. to the reflux temperature of the reaction mixture, the bicyclic acetylene derivative of the formula XIIb is obtained, as shown in Example H3. When left to stand, the compound of the formula XIIb is slowly converted into the more stable monocyclic acetylenecarbinol of the formula VIb. Under the reaction conditions chosen, the latter is converted back completely into the bicyclic acetylene derivative of the formula XIIb which further reacts by itself and is converted in the presence of p-methoxybenzyl(PMB) isocyanate (3) (prepared by introduction of phosgene at 115° C. into a suspension of p-methoxybenzylamine hydrochloride dissolved in chlorobenzene and removal of the resulting isocyanate by distillation at 83° C./0.08 mm Hg) into the p-methoxybenzyl(PMB)-urea derivative of the formula XIIe.

(13) By reduction of the acetylene derivative of the formula XIIe, for example analogously to Synthesis 1973, 457 with an $H_2$-Lindlar catalyst, the ethene derivative of the formula XIIf is formed, which, after ozonolysis and reaction with $(CH_3)_2S$, for example analogously to Tetrahedron Lett. 36, 4273 (1966), gives (14) a tricyclic carbinol intermediate. The latter is converted (15) into the tricyclic compound of the formula VIIIa by standard oxidation methods, for example with $Na_2Cr_2O_7$ in sulfuric acid, and (+)-hydantocidin of the formula Ia is then obtained, for example, in accordance with the reaction steps (6), (7) and (8) shown in equation 3.

Further examples for the preparation of 1',1'-disubstituted and 1'-spiro-nucleosides of the formula I based on the present process according to the invention are shown in equations 5 and 6.

Equation 5:

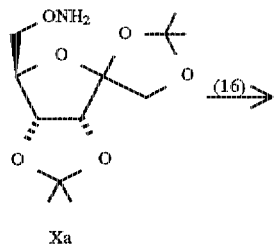

Xa

Equation 5:

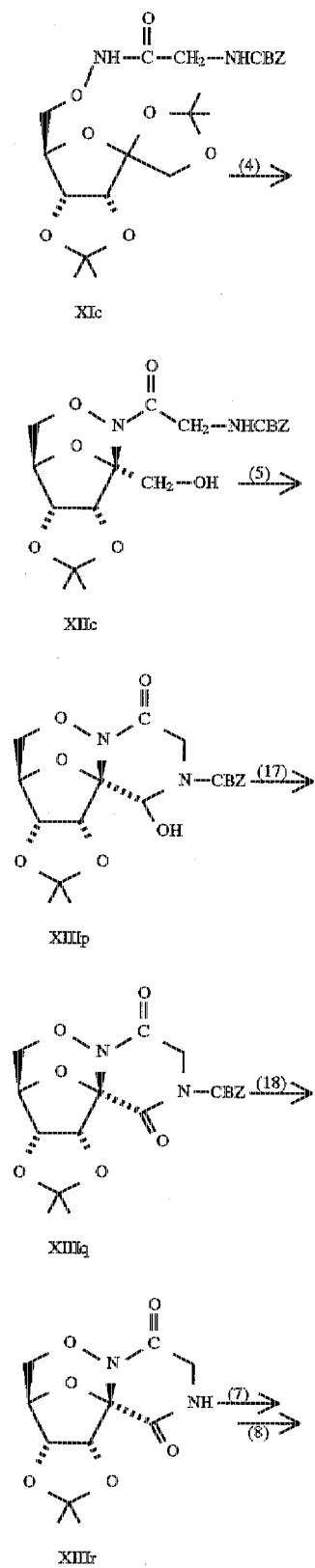

Equation 5:

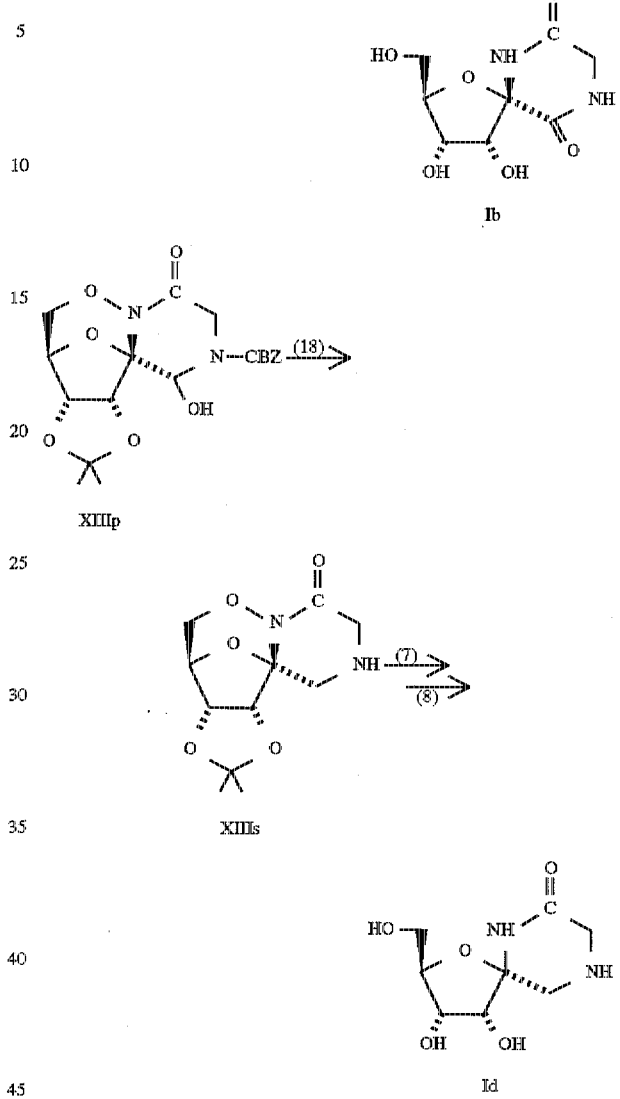

The synthesis according to equation 5 starts from the compound of the formula Xa, which can easily be obtained according to equation 3 from D-fructose via 1',2:3',4'-di-O-isopropylidene-D-psicofuranose of the formula IXa.

(16) The compound of the formula Xa is converted, for example analogously to J. Org. Chem. 26, 2525 (1961), with 1-hydroxy-benzotriazole (HOBT), N-(3-dimethylaminopropyl-N'-ethyl-carbodiimide hydrochloride (EDCI) and glycine-CBZ (Gly-CBZ) in methylene chloride, into the compound of the formula XIc and is then cyclized (4) to the carbinol of the formula XIIc, as described in Preparation Example H2. Subsequent oxidation, for example with Jones reagent (5), as described in equation 3, leads to the tricyclic compound of the formula XIIIp; (MS (DCI—NH$_3$): [M$^{\oplus}$]406, [MS$^{\oplus}$+H]407, [M$^{\oplus}$+NH$_3$]424).

The compound of the formula XIIIp can either be converted either (17) by oxidation, analogously to that described, for example, in J. Am. Chem. Soc. 89, 2416 (1967), into the compound of the formula XIIIq of melting point 186°–187° C. and (18), after removal of the CBZ protective group by standard methods, as described, for example, in J. Org. Chem. 55, 270 (1990), into the compound of the formula XIIIr; $^1$H-NMR (250 MHz, $d_6$-DMSO): 8.40 ppm (s, 1H), 4.98 ppm (d, 1H), 4.90 ppm (d, 1H), 4.48 ppm (s, 1H), 4.15–3.90 ppm (m, 4H), 1.40 ppm (s, 3H), 1.37 ppm (s, 3H), and then give the compound of the formula Ib via reaction steps (7) and (8), as described in equation 3; or

(18) can be converted by means of hydrogenolysis of the CBZ protective group and the free hydroxyl group, as described, for example, in J. Org. Chem. 55, 270 (1990), into the compound of the formula XIIIs; (MS (FAB): [2M$^\oplus$+H]513, [M$^\oplus$+H]257), and subsequently into the compound of the formula Id via reaction steps (7) and (8), as described in equation 3.

Equation 6:

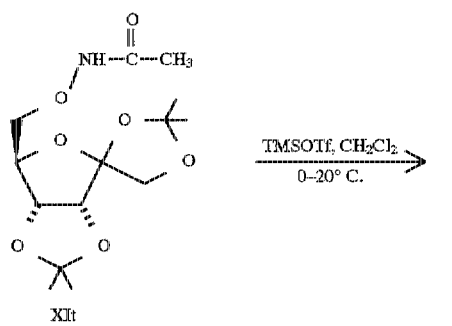

XIt

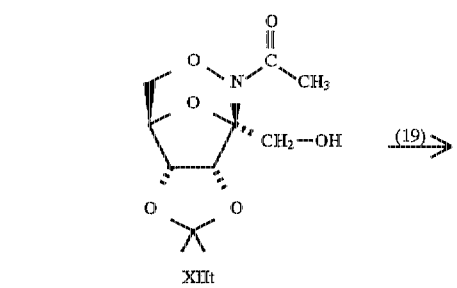

XIIt

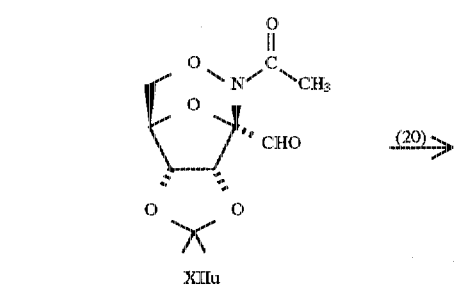

XIIu

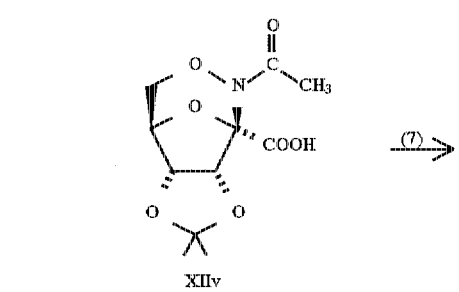

XIIv

-continued

Equation 6:

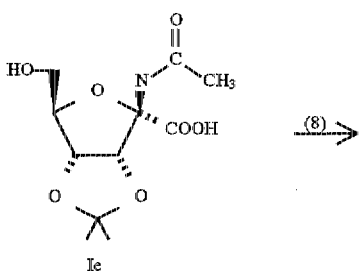

Ie

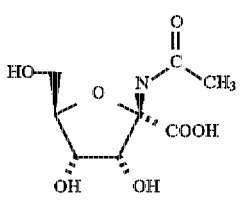

If

The synthesis according to equation 6 starts from the compound of the formula XIt, which can easily be prepared from D-fructose by methods analogous to those described in equation 3.

The cyclization of the compound of the formula XIt to give the bicyclic carbinol of the formula XIIt is described in Preparation Example H4. (19) By Swern oxidation familiar to the expert, as described, for example, in Tetrahedron 34, 1651 (1978), the aldehyde of the formula XIIu is obtained; $^1$H-NMR (250 MHz, CDCl$_3$): 9.42 ppm (s, 1H), 5.18 ppm (d, 1H), 5.00 ppm (d, 1H), 4.55 ppm (s, 1H), 4.15 ppm (d, 1H), 3.87 ppm (d, 1H), 2.18 ppm (s, 3H), 1.56 ppm (s, 3H), 1.38 ppm (s, 3H). After a further oxidation with NaClO$_2$ analogously to J. Org. Chem. 45, 1175 (1980), (20) the carboxylic acid of the formula XIIv of melting point 154°–155° C. is formed. Cleavage of the N—O bond and hydrolysis of the isopropylidene protective group are carried out, for example, analogously to (7) and (8) in equation 3 and gives the 1',1'-disubstituted nucleoside of the formula If of melting point 130°–132° C. (decomposition).

The following examples illustrate the invention in more detail without limiting it.

PREPARATION EXAMPLES

Example H1: Total synthesis of (+)-hydantocidin of the formula Ia:

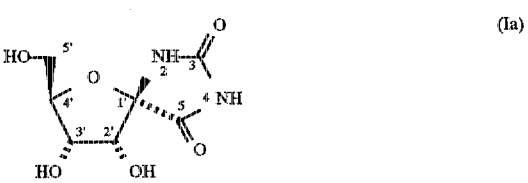

H1.1. Preparation of a compound of the formula VIIa(intermediate)

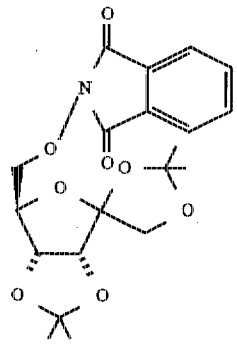
(VIIa)

150.6 ml (0.830 mol) of diethyl azodicarboxylate are added dropwise at 0° C. under a nitrogen atmosphere to a solution of 180 g (0.691 mol) of 1',2:3',4'-di-O-isopropylidene-D-psicofuranose of the formula IXa, 181.2 g (0.691 mol) of triphenylphosphine and 112.8 g (0.691 mol) of N-hydroxyphthalimide in 1.5 l of dry tetrahydrofuran. This reaction mixture is stirred at 20° C. for 5 hours and then concentrated in vacuo. The solid residue is triturated with a mixture of ethyl acetate/hexane ¼ and filtered off and the filtrate is chromatographed by means of flash chromatography and the eluting agent ethyl acetate/hexane ½. 241 g of the desired product of melting point 111°–113° C. are obtained.

H1.2. Preparation of the compound of the formula Xa(intermediate)

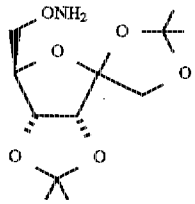
(Xa)

A solution of 32.3 ml (0.666 mol) of hydrazine hydrate in 135 ml of water is added to an ethanolic solution of 225 g (0.555 mol) of the compound of the formula VIIa at 60° C. and the mixture is refluxed for 15 minutes. After cooling, the precipitate is filtered off, the filtrate is concentrated in vacuo and the resulting residue is washed with methylene chloride and filtered off. 149 g of the desired product are obtained as a viscous oil, which can be used directly for the next reaction stage without purification. IR (film): 3340, 3050, 2990, 2940, 2900, 2680, 2410, 2300, 1740, 1590, 1460 and 1420 $cm^{-1}$.

H1.3. Preparation of the compound of the formula XIa(intermediate)

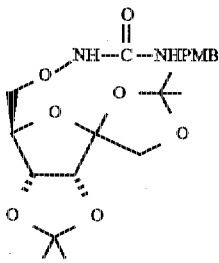
(XIa)

A solution of 70 g (0.254 mol) of the compound of the formula Xa and 43.2 g (0.265 mol) of p-methoxybenzyl isocyanate (PMB-N=C=O) in acetonitrile is stirred at 20° C. for 16 hours and then concentrated in vacuo. Purification by means of flash chromatography and ethyl acetate/hexane 1/1 as the eluting agent gives the desired product in a yield of 105.7 g. MS (FD): $[M^+]438$, $[M^++H]339$, $[M^+—CH_3]$ 423.

H1.4. Preparation of the compound of the formula XIIa(intermediate)

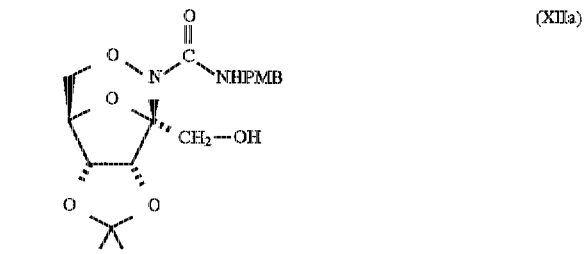
(XIIa)

0.82 ml (4.5 mmol) of trimethylsilyl triflate is added to 20.0 g (45.6 mmol) of an ice-cooled solution of the compound of the formula XIa, in which PMB is the group

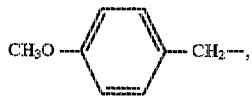

in 1 l of acetonitrile and the mixture is stirred at 20° C. for 16 hours. 5 ml of triethylamine are then added and the solvent is evaporated off. For purification, the residue is filtered over silica gel. 17.0 g of the desired pure product are obtained. MS (FD): $[M^+, 100\%]380$, $[M^++H, 60\%,]381$, $[M^{+—H}, 40\%,]379$.

H1.5. Preparation of the compound of the formula VIIIa(intermediate)

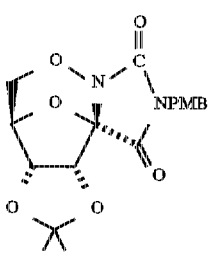
(VIIIa)

Jones reagent, prepared from 111 g (0.372 mol) of $Na_2Cr_2O_7$—$2H_2O$, 68 ml of concentrated sulfuric acid and 372 ml of water, is slowly added at a temperature below 30° C. to 56.0 g (0.149 mol) of the compound of the formula XIIa in 1 l of acetone and the resulting reaction mixture is then further stirred for 24 hours. The precipitate is separated off from the dark brown solution, washed with water and dried. The desired product is obtained as crystals of melting point 192°–194° C.

H1.6. Preparation of the compound of the formula XIIIa(intermediate)

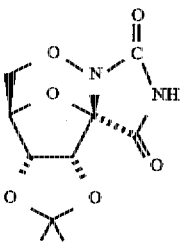
(XIIIa)

530 ml of an aqueous solution of 291.3 g (0.513 mol) of cerium ammonium nitrate (CAN) are added to 20 g (53.1 mmol) of the compound of the formula VIIIa in 1 l of acetonitrile at 20° C. After 10 minutes, the reaction mixture is extracted three times with ethyl acetate and the combined yellowish organic phases are washed with small portions of saturated sodium chloride solution until the yellow colour has disappeared. They are then dried over magnesium sulfate and concentrated in vacuo. The yellow, solid residue is triturated with diethyl ether and filtered off. The desired product is obtained in a yield of 13.5 g as white crystals of melting point 246°–248° C.

H1.7. Preparation of the compound of the formula XIVa(intermediate)

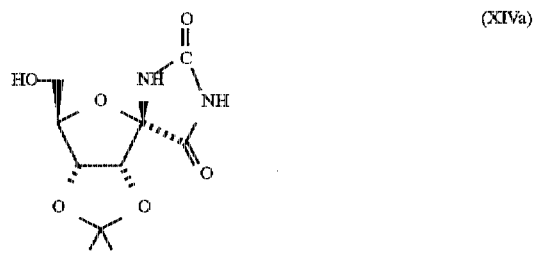

(XIVa)

A mixture of 2.6 g (9.76 mmol) of molybdenum hexacarbonyl $Mo(CO)_6$ and 2.5 g (9.76 mmol) of the compound of the formula XIIIa in 25 ml of a solvent mixture of acetonitrile/water 10/1 is stirred for 12 hours at 90° C. under a nitrogen atmosphere. After cooling, the black suspension is filtered over Celite and the filtrate is concentrated in vacuo. Purification by means of flash chromatography and ethyl acetate as the eluting agent gives 1.92 g of the desired product as crystals of melting point 176°–178° C.

H1.8 Preparation of (+)-hydantocidin of the formula Ia

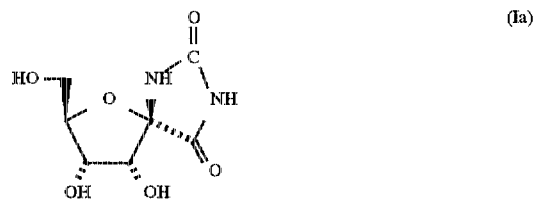

(Ia)

An ice-cooled suspension of 0.50 g (1.93 mmol) of the compound of the formula XIVa and 3 ml of trifluoroacetic acid in 7 ml of water is stirred between 0° and 10° C. until a homogeneous solution forms. The crude mixture is evaporated in vacuo, without being heated, and the residue is recrystallized from methanol/diethyl ether. This gives the desired (+)-hydantocidin in a yield of 0.495 g of melting point 186°–188° C.

FURTHER PREPARATION EXAMPLES

Example H2: Preparation of the compound of the formula XIIc (equation 5)

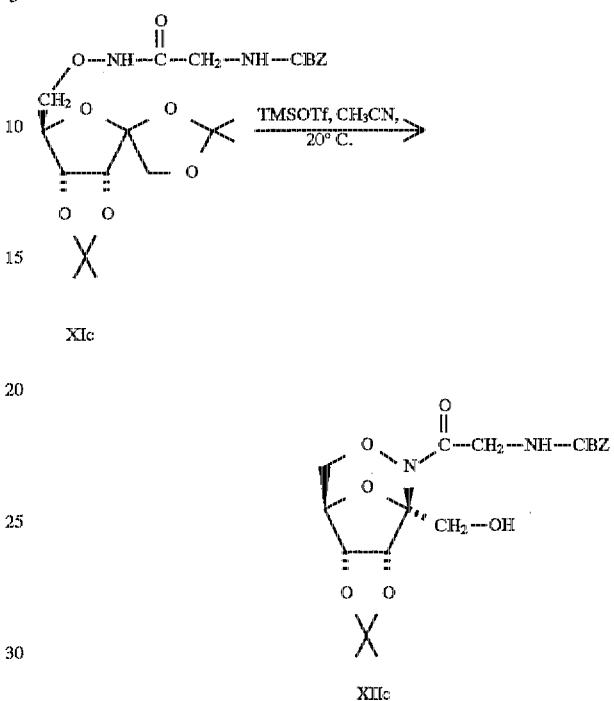

81 μl (0.45 mmol) of trimethylsilyl triflate (TMSOTf) are added to a solution of 2.0 g (4.48 mmol) of the compound of the formula XIc, in which CBZ is the group

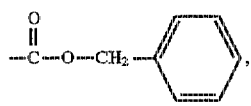

in 200 ml of acetonitrile. After the reaction solution has been stared at 20° C. for 72 hours, 3 drops of triethylamine are added and the mixture is then evaporated in vacuo. Purification is carried out by means of silica gel chromatography and ethyl acetate/methylene chloride ⅓ as the eluting agent. The desired product is obtained in a yield of 1.1 g. $^1$H-NMR (500 MHz, $CDCl_3$): 7.1–7.4 ppm (m, 5H), 5.45 ppm (broad s, 1H), 5.13 ppm (s, 2H), 4.93 ppm (d, 1H), 4.87 ppm (d, 1H), 4.45 ppm (s,1H), 4.28 ppm (dxd, 1H), 4.23–4.02 ppm (m, 4H), 3.88 ppm (m, 1H), 1.53 ppm (s, 3H), 1.39 ppm (s, 3H).

Example H3: Preparation of the compound of the formula XIIb (or VIb) (equation 4)

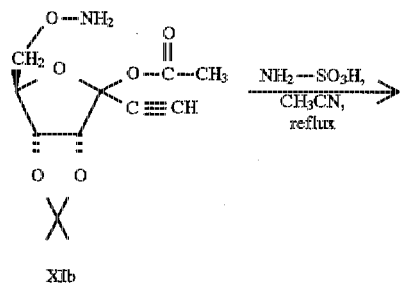

XIb

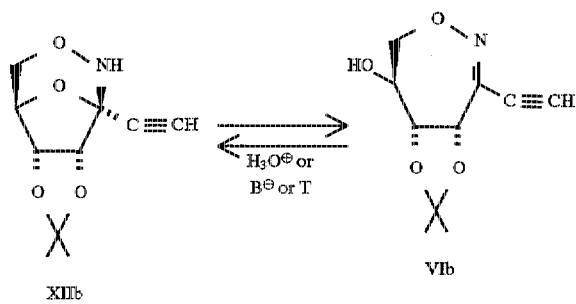

XIIb         VIb 3.0 g (11.06 mmol) of the compound of the formula XIb and a catalytic amount of $NH_2$—$SO_3H$ (about 2 mmol) in 100 ml of nitromethane are refluxed for 30 minutes and the course of the reaction is monitored by means of thin layer chromatography (eluting agent methylene chloride/ethyl acetate 5/1). When the reaction is complete, the reaction solution is evaporated in vacuo and the residue is diluted with methylene chloride and washed successively with 1N aqueous hydrochloric acid, water and saturated sodium bicarbonate solution. The organic phase is dried over magnesium sulfate, filtered and concentrated and the residue is purified by means of flash chromatography and methylene chloride/ethyl acetate 5/1 as the eluting agent. The bicyclic compound of the formula XIIb is thereby obtained first as the kinetically controlled product as an oil in a yield of 1.28 g. $^1$H-NMR (500 MHz, $CDCl_3$): 5.38 ppm (s, 1H), 5.00 ppm (d, 1H), 4.92 ppm (d, 1H), 4.36 ppm (s, 1H), 4.00 ppm (dxd, 1H), 3.68 ppm (dxd, 1H), 2.70 ppm (s, 1H), 1.56 ppm (s, 3H), 1.43 ppm (s, 3H).

When left to stand, this compound converts slowly into the thermodynamically more stable monocyclic compound of the formula VIb: IR (KBr): 3500, 3240, 2990, 2100, 1575, 1470, 1440, 1410, 1385 cm$^{-1}$.

The bicyclic compound of the formula XIIb is formed again by treatment of the compound of the formula VIb with dilute acid ($H_3O^{\oplus}$) or base ($B^{\ominus}$) or by gentle heating (T).

Example H4: Preparation of the compound of the formula XiiT (equation 6)

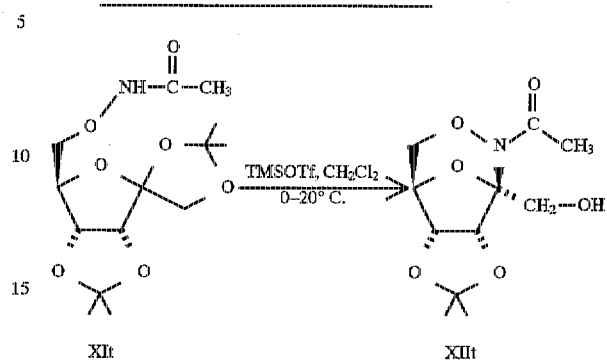

XIt         XIIt

11 μl (0.063 mmol) of trimethylsilyl triflate (TMSOTf) are added to a solution of 0.10 g (0.315 mmol) of the compound of the formula XIt in methylene chloride at 0° C. and the mixture is stirred at 20° C. for 12 hours. 5 drops of triethylamine are then added to the reaction solution and the mixture is evaporated in vacuo. For purification, the resulting residue is triturated in a mixture of ethyl acetate/hexane 4/1 and the resulting white crystalline product is filtered off. $^1$H-NMR (250 MHz, $CDCl_3$): 4.94 ppm (d, 1H), 4.86 ppm (d, 1H), 4.42 ppm (s, 1H), 4.30–4.00 ppm (m, 4H), 3.85 ppm (dxd, 1H), 2.15 ppm (s, 3H), 1.52 ppm (s, 3H), 1.40 ppm (s, 3H).

Example H5: Standard Wittig reaction with the compound of the formula XIIIa

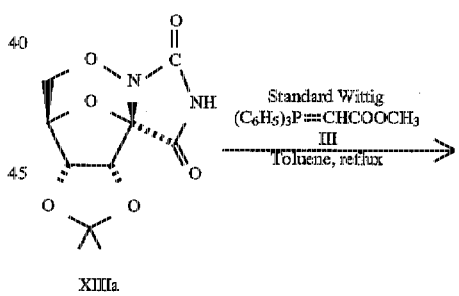

XIIIa

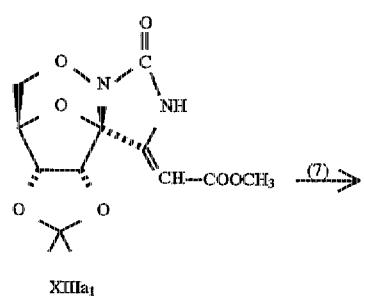

XIIIa$_1$

XIVa₁

Ia₁

The tricyclic compound of the formula XIIIa is reacted under standard Wittig conditions with an equimolar amount of the reagent methyl (triphenylphosphoranylidene)acetate of the formula III $(C_6H_5)_3P=CHCOOCH_3$ (III) in refluxing toluene to give the compound of the formula XIIIa1; melting point 173°–174° C.

(7) Cleavage of the N—O bond in the compound of the formula XIIIa₁ analogously to that described in equation 3 leads to the compound of the formula XIVa₁;
$^1$H-NMR (360 MHz, $d_6$-DMSO): 9.55 ppm (s, 1H), 8.15 ppm (s, 1H), 5.25 ppm (s, 1H), 5.05 ppm (s, 1H), 4.82 ppm (dxd, 1H), 4.64 ppm (d, 1H), 4.12 ppm (m, 1H), 3.65 ppm (s, 3H), 3.52 ppm (m, 2H), 1.48 ppm (s, 3H), 1.28 ppm (s, 3H).

(8) Hydrolysis of the compound of the formula XIVa₁ analogously to that described in equation 3 leads to the (+)-hydantoin derivative of the formula Ia₁.

What is claimed is:

1. A process for the preparation of a compound of the formula I (I)

in which

A is the group $$\begin{array}{c} H\ H \\ |\ \ | \\ -C-C- \\ |\ \ | \\ R_1\ R_2 \end{array}$$

or —CH=CH—;

$R_1$ is hydrogen, halogen, hydroxyl, $C_1$–$C_4$alkoxy, $C_1$–$C_4$alkoxy-$C_1$–$C_4$alkoxy, tri-$C_1$–$C_6$alkylsilyloxy, benzyloxy or phenoxy which are unsubstituted or substituted by $C_1$–$C_4$alkyl, $C_1$–$C_4$haloalkyl, halogen, cyano or nitro, $R_{10}$—C(O)—O—, $R_3(R_4)N$—, azido, cyano or $L_1$—O—,
wherein $L_1$ is a protective group;

$R_2$ is hydrogen, halogen, hydroxyl, $C_1$–$C_4$alkoxy, $C_1$–$C_4$alkoxy-$C_1$–$C_4$alkoxy, tri-$C_1$–$C_6$alkylsilyloxy, benzyloxy or phenoxy which are unsubstituted or substituted by $C_1$–$C_4$alkyl, $C_1$–$C_4$haloalkyl, halogen, cyano or nitro, $R_{10}$—C(O)—O—, $R_3(R_4)N$—, azido, cyano or $L_1$—O—, wherein $L_1$ is a protective group, with the proviso that only one of the substituents $R_1$ or $R_2$ is azido; or $R_1$ together with $R_2$ is —OSi($R_{11}$)$R_{20}$O— or —OC($R_{12}$)$R_{21}$O—;

$R_3$ is hydrogen, unsubstituted or substituted $C_1$–$C_{10}$alkyl, $C_3$–$C_{10}$alkenyl or $C_3$–$C_{10}$alkynyl, formyl, $C_1$–$C_{10}$alkylcarbonyl which is unsubstituted or substituted by halogen, hydroxyl, $C_1$–$C_4$alkoxy, $C_1$–$C_4$alkylamino, di-$C_1$–$C_4$alkylamino, cyano, $C_1$–$C_4$alkoxycarbonyl, carbamoyl, $C_1$–$C_4$alkylaminocarbonyl, di-$C_1$–$C_4$alkylaminocarbonyl or phenyl, $C_3$–$C_{10}$alkenylcarbonyl, $C_3$–$C_{10}$alkynylcarbonyl, $C_1$–$C_{10}$alkoxycarbonyl or phenoxycarbonyl or benzyloxycarbonyl which are unsubstituted or substituted by halogen, $C_1$–$C_4$alkyl, $C_1$–$C_4$haloalkyl, $C_1$–$C_4$alkoxy or $C_1$–$C_4$haloalkoxy;

$R_4$ is hydrogen, unsubstituted or substituted $C_1$–$C_{10}$alkyl, $C_3$–$C_{10}$alkenyl or $C_3$–$C_{10}$alkynyl, formyl, $C_1$–$C_{10}$alkylcarbonyl which is unsubstituted or substituted by halogen, hydroxyl, $C_1$–$C_4$alkoxy, $C_1$–$C_4$alkylamino, di-$C_1$–$C_4$alkylamino, cyano, $C_1$–$C_4$alkoxycarbonyl, carbamoyl, $C_1$–$C_4$alkylaminocarbonyl, di-$C_1$–$C_4$alkylaminocarbonyl or phenyl, $C_3$–$C_{10}$alkenylcarbonyl, $C_3$–$C_{10}$alkynylcarbonyl, $C_1$–$C_{10}$-alkoxycarbonyl or phenoxycarbonyl or benzyloxycarbonyl which are unsubstituted or substituted by halogen, $C_1$–$C_4$alkyl, $C_1$–$C_4$haloalkyl, $C_1$–$C_4$alkoxy or $C_1$–$C_4$haloalkoxy, with the proviso that only one of the substituents $R_3$ or $R_4$ is formyl; or $R_3$ together with $R_4$ is —(CH$_2$)$_n$—, —(CH$_2$)$_o$—O—(CH$_2$)$_p$—, —(CH$_2$)$_o$—S—(CH$_2$)$_p$— or —(CH$_2$)$_o$—NH—(CH$_2$)$_p$—, which can be unsubstituted or substituted by $C_1$–$C_4$alkyl;

n is 4, 5 or 6;

o is 1,2, 3 or 4;

p is 1, 2, 3 or 4; and the sum of o and p is 3, 4 or 5;

$R_{10}$ is hydrogen, $C_1$–$C_4$alkyl or benzyl or phenyl which are unsubstituted or substituted by $C_1$–$C_4$alkyl, $C_1$–$C_4$alkoxy, $C_1$–$C_4$haloalkyl, halogen or cyano;

$R_{11}$ is $C_1$–$C_4$alkyl or phenyl;

$R_{20}$ is $C_1$–$C_4$alkyl; or $R_{11}$ together with $R_{20}$ is —(CH$_2$)$_{n3}$—;

$R_{12}$ is hydrogen, $C_1$–$C_4$alkyl or phenyl;

$R_{21}$ is hydrogen or $C_1$–$C_4$alkyl; or $R_{12}$ together with $R_{21}$ is —(CH$_2$)$_{n3}$—;

$n_3$ is 4, 5 or 6;

$R_8$ is unsubstituted or substituted $C_1$-$C_{10}$alkyl, $C_2$-$C_{10}$alkenyl, $C_2$-$C_{10}$alkynyl, $C_1$-$C_{10}$alkyl-C(Q)—, $C_2$-$C_{10}$alkenyl-C(Q)—, $C_2$-$C_{10}$alkynyl-C(Q)—, $C_2$-$C_{10}$alkenyloxycarbonyl, $C_2$-$C_{10}$alkynyloxycarbonyl, phenoxycarbonyl or benzyloxycarbonyl, cyano, carboxyl, phenyl, nitro, $C_1$-$C_{10}$alkoxycarbonyl, $R_3(R_4)$N—C(O)— or $L_2$—NH—$C_1$-$C_{10}$alkyl, wherein $L_2$ is a protective group;

$R_9$ is hydrogen, unsubstituted or substituted $C_2$-$C_{10}$alkyl, $C_2$-$C_{10}$alkenyl, $C_2$-$C_{10}$alkynyl, $C_1$-$C_{10}$alkyl-C(Q)—, $C_2$-$C_{10}$alkenyl-C(Q)—, $C_2$-$C_{10}$alkynyl-C(Q)—, phenyl, benzyl, phenyl-C(Q)—, phenoxycarbonyl, benzyloxycarbonyl, phenoxycarbonyl-$C_1$-$C_{10}$alkyl or benzyloxycarbonyl-$C_1$-$C_{10}$alkyl, $C_1$-$C_4$alkoxycarbonyl, $C_1$-$C_4$alkoxy-C(O)—NH—SO$_2$—, NH$_2$—SO$_2$—, $R_{18}(R_{19})$N—C(Q)—, $R_3(R_4)$N—C(O)—$C_1$-$C_{10}$alkyl, $C_1$-$C_4$alkoxy-NH—C(O)—, phenoxy-NH—C(O)— or benzyloxy-NH—C(O)—; or $R_8$ and $R_9$ together form a ring —X—Y—Z—, in which X is the groups $C_1$-$C_3$alkylene

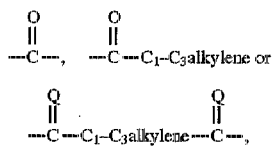

wherein the alkylene chain can be unsubstituted or substituted by halogen, hydroxyl, $C_1$-$C_4$alkoxy, amino, $C_1$-$C_4$alkylamino, di-$C_1$-$C_4$alkylamino, cyano, carboxyl, $C_1$-$C_4$alkoxycarbonyl, $C_1$-$C_4$alkylcarbonyloxy, carbamoyl, $C_1$-$C_4$alkylaminocarbonyl, di-$C_1$-$C_4$alkylaminocarbonyl or phenyl;

Q is oxygen or sulfur;

Y is oxygen, $C_1$— or $C_2$-alkylene which is unsubstituted or substituted by $C_1$-$C_4$alkyl or —NR$_5$—;

Z is the groups $C_1$-$C_3$alkylene,

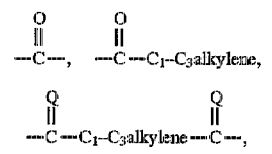

wherein the alkylene chain can be unsubstituted or substituted by halogen, hydroxyl, $C_1$-$C_4$alkoxy, amino, $C_1$-$C_4$alkylamino, di-$C_1$-$C_4$alkylamino, cyano, carboxyl, $C_1$-$C_4$alkoxycarbonyl, carbamoyl, $C_1$-$C_4$alkylaminocarbonyl, di-$C_1$-$C_4$alkylaminocarbonyl or phenyl,

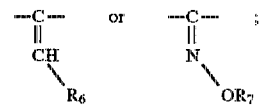

or

Y and Z together are a group

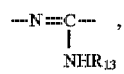

wherein bonding to the ring C atom takes place via the C atom;

$R_5$ is hydrogen, unsubstituted or substituted $C_1$-$C_{10}$alkyl, $C_3$-$C_{10}$alkenyl, $C_3$-$C_{10}$alkynyl, $C_3$-$C_{10}$alkenylcarbonyl or $C_3$-$C_{10}$alkynylcarbonyl, formyl, $C_1$-$C_{10}$alkylcarbonyl which is unsubstituted or substituted by halogen, hydroxyl, $C_1$-$C_4$alkoxy, amino, $C_1$-$C_4$alkylamino, di-$C_1$-$C_4$alkylamino, cyano, $C_1$-$C_4$alkoxycarbonyl, carbamoyl, $C_1$-$C_4$alkylaminocarbonyl, di-$C_1$-$C_4$alkylaminocarbonyl or phenyl, $C_1$-$C_{10}$alkoxycarbonyl or phenoxycarbonyl, benzylcarbonyl, benzyloxycarbonyl or phenyl which are unsubstituted or substituted by halogen, $C_1$-$C_4$alkyl, $C_1$-$C_4$haloalkyl, $C_1$-$C_4$alkoxy or $C_1$-$C_4$haloalkoxy;

$R_6$ is unsubstituted or substituted $C_1$-$C_{10}$alkyl, carboxyl, $C_1$-$C_4$alkoxycarbonyl, carbamoyl, $C_1$-$C_4$alkylaminocarbonyl or di-$C_1$-$C_4$alkylaminocarbonyl;

$R_7$ is hydrogen, $C_3$-$C_7$cycloalkyl or unsubstituted or substituted $C_1$-$C_{10}$alkyl, $C_2$-$C_{10}$alkenyl, $C_3$-$C_{10}$alkynyl or benzyl;

$R_{13}$ is hydrogen or unsubstituted or substituted $C_1$-$C_{10}$alkyl, $C_1$-$C_{10}$alkylcarbonyl, phenyl or benzyl;

$R_{16}$ is $C_1$-$C_5$alkyl, $C_3$-$C_5$alkenyl, phenyl or benzyl;

$R_{18}$ is unsubstituted or substituted $C_1$-$C_{10}$alkyl, $C_1$-$C_{10}$alkoxycarbonyl, phenoxycarbonyl, benzyl, benzyloxycarbonyl, $C_1$-$C_6$alkylcarbonyl, $C_1$-$C_4$alkylaminocarbonyl, di-$C_1$-$C_4$alkylaminocarbonyl or $L_2$; and $R_{19}$ is hydrogen, formyl, $C_1$-$C_{10}$alkylcarbonyl which is unsubstituted or substituted by halogen, hydroxyl, $C_1$-$C_4$alkoxy, amino, $C_1$-$C_4$alkylamino, di-$C_1$-$C_4$alkylamino, cyano, carboxyl, $C_1$-$C_4$alkoxycarbonyl, carbamoyl, $C_1$-$C_4$alkylaminocarbonyl, di-$C_1$-$C_4$alkylaminocarbonyl or phenyl, $C_3$-$C_{10}$alkenylcarbonyl, $C_3$-$C_{10}$alkynylcarbonyl, $C_1$-$C_{10}$alkoxycarbonyl, phenoxycarbonyl, benzyl, benzyloxycarbonyl, $C_1$-$C_4$alkylaminocarbonyl, di-$C_1$-$C_4$alkylaminocarbonyl or $L_2$, or salts of these compounds, which comprises a) cyclizing the compound of the formula XI

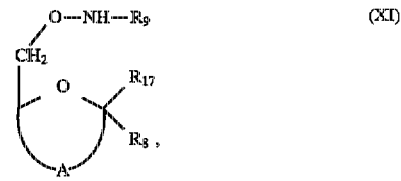

in which

A, $R_8$ and $R_9$ are as defined, but A is other than

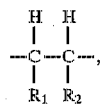

if $R_1$ and $R_2$ simultaneously are hydroxyl or $H_2N-$ and $R_{17}$ is halogen, hydroxyl, $C_1-C_{10}$alkoxy, unsubstituted or substituted $C_1-C_{10}$alkyl—C(O)O—, benzyloxy or benzoyloxy, $CF_3C(O)O-$, $C_1-C_{10}$alkoxy-C(O)O—, $C_1-C_6$alkylsulfonyloxy, phenylsulfonyloxy, $CF_3S(O)_2O-$ or a group $L_1-O-$, wherein $L_1$ is a protective group; or $R_{17}$ and $R_8$ together form a group

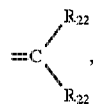

$=N-OR_7$, $-O-CH(R_6)-$ or $-O-C(R_{12})R_{21}-O-CH_2-$; and the radicals $R_{22}$ independently of one another are fluorine, chlorine, bromine, unsubstituted or substituted $C_1-C_{10}$alkyl, carboxyl, $C_1-C_4$alkoxycarbonyl, carbamoyl, $C_1-C_4$alkylaminocarbonyl or di-$C_1-C_4$alkylaminocarbonyl;

into the compound of the formula XII

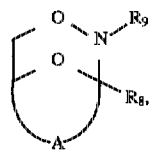 (XII)

in which

A, $R_8$ and $R_9$ are as defined, and subsequently $b_1$) splitting the N—O bond in the compound of the formula XII by hydrogenolysis or with an organometallic compound to give 1',1'-disubstituted nucleosides of the formula I, or $b_2$) first cyclizing the compound of the formula XII, in which $R_8$ and $R_9$ are as defined, with the exception of $C_1-C_{10}$alkyl, $C_2-C_{10}$alkenyl, $C_2-C_{10}$alkynyl, phenyl or benzyl, to give the compound of the formula XIII

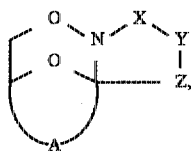 (XIII)

in which A, X, Y and Z are as defined, in a manner known per se, and subsequently splitting the N—O bond by hydrogenolysis or with an organometallic compound to give 1'-spiro-nucleosides of the formula I.

2. A process according to claim 1, in which

A is the group

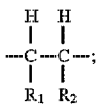

$R_1$ is hydroxyl, $C_1-C_4$alkoxy, $C_1-C_4$alkoxy-$C_1-C_4$alkoxy, trimethylsilyloxy, tert-butyl-dimethylsilyloxy or benzyloxy or phenoxy which are unsubstituted or substituted by $C_1-C_4$alkyl, $C_1-C_4$haloalkyl, halogen, cyano or nitro; $R_{10}-C(O)-O-$,

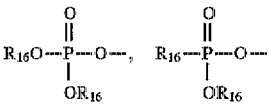

or $L_1-O-$;

$R_2$ is hydroxyl, $C_1-C_4$alkoxy, $C_1-C_4$alkoxy-$C_1-C_4$alkoxy, trimethylsilyloxy, tert-butyl-dimethylsilyloxy, benzyloxy or phenoxy which are unsubstituted or substituted by $C_1-C_4$alkyl, $C_1-C_4$haloalkyl, halogen, cyano or nitro, $R_{10}-C(O)-O-$ or $L_1-O-$; or $R_1$ together with $R_2$ is $-OSi(R_{11})R_{20}O-$ or $-OC(R_{12})R_{21}O-$;

$R_3$ is hydrogen, unsubstituted $C_1-C_{10}$alkyl, $C_1-C_{10}$alkylcarbonyl, $C_1-C_{10}$alkoxycarbonyl, phenoxycarbonyl or benzyloxycarbonyl;

$R_4$ is hydrogen or unsubstituted $C_1-C_{10}$alkyl;

$R_{10}$ is $C_1-C_4$alkyl or benzyl or phenyl which are unsubstituted or substituted by $C_1-C_4$alkyl, $C_1-C_4$alkoxy, $C_1-C_4$haloalkyl, halogen or cyano;

$R_{11}$ is $C_1-C_4$alkyl or phenyl;

$R_{20}$ is $C_1-C_4$alkyl;

$R_{12}$ is hydrogen or $C_1-C_4$alkyl;

$R_{21}$ is $C_1-C_4$alkyl;

$R_8$ is $C_1-C_{10}$alkyl, $C_2-C_{10}$alkenyl, $C_2-C_{10}$alkynyl, $C_1-C_{10}$alkyl-C(Q)—, phenoxycarbonyl, benzyloxycarbonyl, $C_1-C_{10}$alkoxycarbonyl or $L_2-NH-$,$C_1-C_{10}$alkyl;

$R_9$ is hydrogen, $C_1-C_{10}$alkyl-C(Q)—, benzyl, phenyl-C(Q)—, phenoxycarbonyl, $C_1-C_4$alkoxycarbonyl, $R_{18}(R_{19})N-C(Q)-$ or $R_3(R_4)N-C(O)-C_1-C_{10}$-alkyl; or $R_8$ and $R_9$ together form a ring $-X-Y-Z-$, in which X is the groups

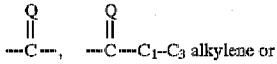

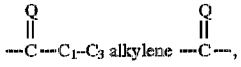

wherein the alkylene chain can be unsubstituted or substituted by halogen, hydroxyl, $C_1-C_4$alkoxy or $C_1-C_4$alkoxycarbonyl;

Q is oxygen;

Y is oxygen, unsubstituted $C_1-$ or $C_2$-alkylene or $-NR_5-$;

Z is the groups $$-\overset{Q}{\underset{\|}{C}}-, \quad -\overset{Q}{\underset{\|}{C}}-C_1-C_3\text{alkylene or}$$

$$-\overset{Q}{\underset{\|}{C}}-C_1-C_3\text{alkylene}-\overset{Q}{\underset{\|}{C}}-,$$

wherein the alkylene chain can be unsubstituted or substituted by halogen, hydroxyl, $C_1-C_4$alkoxy or $C_1-C_4$alkoxycarbonyl, or is $$-\underset{\underset{OR_7}{\overset{\|}{N}}}{\overset{}{C}}-;$$

or Y and Z together are a group $$-N=\underset{NHR_{13}}{\overset{}{C}}-;$$

$R_5$ is hydrogen, $C_1-C_{10}$alkyl or unsubstituted phenoxycarbonyl, benzyloxycarbonyl, benzylcarbonyl or phenyl;

$R_7$ is hydrogen, $C_3-C_7$cycloalkyl, $C_1-C_{10}$alkyl or $C_3-C_{10}$alkynyl;

$R_{13}$ is hydrogen or $C_1-C_4$alkyl;

$R_{16}$ is $C_1-C_5$alkyl, phenyl or benzyl;

$R_{18}$ is unsubstituted $C_1-C_{10}$alkyl, $C_1-C_{10}$alkoxycarbonyl, benzyl, benzyloxycarbonyl or $C_1-C_6$alkylcarbonyl; and $R_{19}$ is hydrogen.

3. A process according to claim 2, in which $R_1$ is hydroxyl, $C_1-C_4$alkoxy, trimethylsilyloxy, unsubstituted benzyloxy, $R_{10}-C(O)-O-$, $$R_{16}O-\underset{\underset{OR_{16}}{|}}{\overset{\overset{O}{\|}}{P}}-O- \text{ or } R_{16}-\underset{\underset{OR_{16}}{|}}{\overset{\overset{O}{\|}}{P}}-O-;$$

$R_2$ is hydroxyl $C_1-C_4$alkoxy, trimethylsilyloxy, unsubstituted benzyloxy, $R_{10}-C(O)-O-$ or $L_1-O-$; or $R_1$ together with $R_2$ is $-OSi(R_{11})R_{20}O-$ or $-OC(R_{12})R_{21}O-$;

$R_{10}$ is $C_1-C_4$alkyl or unsubstituted phenyl;

$R_{11}$ and $R_{20}$ are $C_1-C_4$alkyl;

$R_{12}$ and $R_{21}$ are $C_1-C_4$alkyl;

$R_8$ is $C_1-C_{10}$alkyl, $C_2-C_{10}$alkenyl, $C_2-C_{10}$alkynyl, $C_1-C_{10}$alkyl-$C(Q)-$ or $C_1-C_{10}$alkoxycarbonyl;

$R_9$ is hydrogen, $C_1-C_{10}$alkyl-$C(Q)-$, $C_1-C_4$alkoxycarbonyl, phenoxycarbonyl or $R_{18}(R_{19})N-C(Q)-$; or $R_8$ and $R_9$ together form a ring $-X-Y-Z-$, in which X is the group $$-\overset{Q}{\underset{\|}{C}}- \text{ or } -\overset{Q}{\underset{\|}{C}}-C_1-C_3\text{alkylene},$$

wherein the alkylene chain can be unsubstituted or substituted by halogen or hydroxyl;

Y is oxygen or $-NR_5-$;

Z is the groups $$-\overset{Q}{\underset{\|}{C}}-, \quad -\overset{Q}{\underset{\|}{C}}-C_1-C_3\text{alkylene},$$

wherein the alkylene chain can be unsubstituted or substituted by halogen or hydroxyl, or is $$-\underset{\underset{OR_7}{\overset{\|}{N}}}{\overset{}{C}}-;$$

or Y and Z together are a group $$-N=\underset{NHR_{13}}{\overset{}{C}}-;$$

$R_5$ is hydrogen or unsubstituted $C_1-C_{10}$alkyl;

$R_7$ is hydrogen, $C_3-C_7$cycloalkyl or unsubstituted $C_1-C_{10}$alkyl;

$R_{16}$ is $C_1-C_5$alkyl or benzyl;

$R_{18}$ is unsubstituted $C_1-C_{10}$alkyl or $C_1-C_6$alkylcarbonyl; and $R_{19}$ is a hydrogen.

4. A process according to claim 3, in which $R_1$ is hydroxyl, unsubstituted benzyloxy or $$R_{16}O-\underset{\underset{OR_{16}}{|}}{\overset{\overset{O}{\|}}{P}}-O-;$$

$R_2$ is hydroxyl or unsubstituted benzyloxy;

$R_8$ and $R_9$ together form a ring $-X-Y-Z-$, in which

X is the group $$-\overset{Q}{\underset{\|}{C}}-;$$

Y is $-NR_5-$;

Z is the group $$-\overset{Q}{\underset{\|}{C}}- \text{ or } -\underset{\underset{OR_7}{\overset{\|}{N}}}{\overset{}{C}}-;$$

$R_5$ is hydrogen or unsubstituted $C_1-C_4$alkyl; and $R_7$ is hydrogen or unsubstituted $C_1$–$C_{10}$alkyl.

5. A process according to claim 1, in which
A is the group

$R_1$ is hydroxyl, $C_1$–$C_4$alkoxy, trimethylsilyloxy, unsubstituted benzyloxy, $R_{10}$—C(O)—O—,

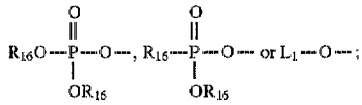

$R_2$ is hydroxyl, $C_1$–$C_4$alkoxy, trimethylsilyloxy, unsubstituted benzyloxy, $R_{10}$—C(O)—O— or $L_1$—O—; or
$R_1$ together with $R_2$ is —OSi($R_{11}$)$R_{20}$O— or —OC($R_{12}$)$R_{21}$—O—;
$R_{10}$ is $C_1$–$C_4$alkyl or unsubstituted phenyl;
$R_{11}$ and $R_{20}$ are $C_1$–$C_4$alkyl;
$R_{12}$ and $R_{21}$ are $C_1$–$C_4$alkyl;
$R_8$ and $R_9$ together for a ring —X—Y—Z—,
in which
X is the group

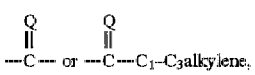

wherein
the alkylene chain can be unsubstituted or substituted by halogen or hydroxyl;
Q is oxygen;
Y is oxygen or —NR$_5$—;
Z is the groups

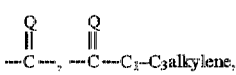

wherein
the alkylene chain can be unsubstituted or substituted by halogen or hydroxyl, or is

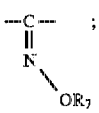

or
Y and Z together are a group

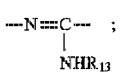

$R_5$ is hydrogen or unsubstituted $C_1$–$C_{10}$alkyl;
$R_7$ is hydrogen, $C_3$–$C_7$cycloalkyl or unsubstituted $C_1$–$C_{10}$alkyl;
$R_{13}$ is hydrogen or unsubstituted $C_1$–$C_{10}$alkyl or $C_1$–$C_{10}$alkylcarbonyl; and
$R_{16}$ is $C_1$–$C_5$alkyl or benzyl.

6. A process according to claim 5, in which $R_1$ and $R_2$ are hydroxyl;
$R_8$ and $R_9$ together form a ring —X—Y—Z—, in which
X and Z are the group

Y is —NR$_5$—;
Q is oxygen; and
$R_8$ is hydrogen.

7. A process according to claim 1, in which
A is the group

or —CH═CH—;

$R_1$ is hydroxyl, $C_1$–$C_4$alkoxy-$C_1$–$C_4$alkoxy, unsubstituted benzyloxy, $R_{10}$—C(O)—O—, $R_3$($R_4$)N—,

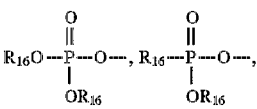

azido or $L_1$—O—;
$R_2$ is hydrogen, halogen, $R_3$($R_4$)N—, azido or cyano;
$R_3$ is hydrogen, unsubstituted or substituted $C_1$–$C_{10}$alkyl, $C_1$–$C_{10}$alkylcarbonyl which is unsubstituted or substituted by hydroxyl, cyano or $C_1$–$C_4$alkylaminocarbonyl, $C_1$–$C_{10}$alkoxycarbonyl or unsubstituted benzyloxycarbonyl;
$R_4$ is hydrogen, unsubstituted or substituted $C_1$–$C_{10}$alkyl, $C_1$–$C_{10}$alkylcarbonyl which is unsubstituted or substituted by hydroxyl, cyano or $C_1$–$C_{C4}$alkylaminocarbonyl, $C_1$–$C_{10}$alkoxycarbonyl or unsubstituted benzyloxycarbonyl;
$R_{10}$ is $C_1$–$C_4$alkyl or unsubstituted benzyl or phenyl;
$R_8$ is unsubstituted or substituted $C_1$–$C_{10}$alkyl, $C_2$–$C_{10}$alkenyl, $C_2$–$C_{10}$alkynyl, $C_1$–$C_{10}$alkyl-C(Q)— or benzyloxycarbonyl, cyano, carboxyl, nitro, $C_1$–$C_{10}$alkoxycarbonyl, $R_3$($R_4$)N—C(O)— or $L_2$—NH—$C_1$–$C_{10}$alkyl;
$R_9$ is hydrogen, unsubstituted or substituted $C_1$–$C_{10}$alkyl, $C_2$–$C_{10}$alkenyl, $C_2$–$C_{10}$alkynyl, $C_1$–$C_{10}$alkyl-C(Q)—, phenoxycarbonyl, benzyloxycarbonyl, phenoxycarbonyl-$C_1$–$C_{10}$alkyl or benzyloxycarbonyl-$C_1$–$C_{10}$alkyl, $C_1$–$C_4$alkoxycarbonyl, $C_1$–$C_4$alkoxy-C(O)—NH—SO$_2$—, NH$_2$—SO$_2$—, $R_{18}$($R_{19}$)N—C(Q)— or $R_3$($R_4$)N—C(O)—$C_1$–$C_{10}$-alkyl; or
$R_8$ and $R_9$ together for a ring —X—Y—Z—,
in which
X is the groups

-continued $$-\overset{Q}{\underset{\|}{C}}-C_1-C_3\text{alkylene}-\overset{Q}{\underset{\|}{C}}-,$$

wherein
the alkylene chain can be unsubstituted or substituted by hydroxyl, amino, $C_1$–$C_4$alkylamino, cyano, carboxyl, $C_1$–$C_4$alkoxycarbonyl, carbamoyl or $C_1$–$C_4$alkylaminocarbonyl;
Q is oxygen;
Y is oxygen or —$NR_5$—;
Z is the groups $$-\overset{Q}{\underset{\|}{C}}-, \quad -\overset{Q}{\underset{\|}{C}}-C_1-C_3\text{alkylene or}$$

$$-\overset{Q}{\underset{\|}{C}}-C_1-C_3\text{alkylene}-\overset{Q}{\underset{\|}{C}}-,$$

wherein
the alkylene chain can be unsubstituted or substituted by hydroxyl, amino, $C_1$–$C_4$alkylamino, cyano, carboxyl, $C_1$–$C_4$alkoxycarbonyl, carbamoyl or $C_1$–$C_4$alkylaminocarbonyl; or
Y and Z together are a group $$-N=C-;$$
$$\quad\quad |$$
$$\quad\quad NHR_{13}$$

$R_5$ is hydrogen, unsubstituted $C_1$–$C_{10}$alkylcarbonyl, $C_1$–$C_{10}$alkoxycarbonyl, phenoxycarbonyl, benzylcarbonyl, benzyloxycarbonyl or phenyl;
$R_6$ is carboxyl or $C_1$–$C_4$alkoxycarbonyl;
$R_7$ is hydrogen, unsubstituted or substituted $C_1$–$C_{10}$alkyl or benzyl;
$R_{13}$ is hydrogen or unsubstituted or substituted $C_1$–$C_{10}$alkyl, $C_1$–$C_{10}$alkylcarbonyl, phenyl or benzyl;
$R_{16}$ is $C_1$–$C_5$alkyl, $C_3$–$C_5$alkenyl, phenyl or benzyl;
$R_{18}$ is $C_1$–$C_{10}$alkoxycarbonyl, phenoxycarbonyl, benzyl, benzyloxycarbonyl or $C_1$–$C_6$alkylcarbonyl; and
$R_{19}$ is hydrogen, unsubstituted $C_1$–$C_{10}$alkylcarbonyl, $C_1$–$C_{10}$alkoxycarbonyl, phenoxycarbonyl, benzyl, benzyloxycarbonyl or $C_1$–$C_4$alkylaminocarbonyl.

8. A process according to claim 7, in which
A is the group $$-\overset{H}{\underset{R_1}{\overset{|}{C}}}-\overset{H}{\underset{R_2}{\overset{|}{C}}}-;$$

$R_1$ is hydroxyl, $R_3(R_4)N$—, $$R_{16}O-\overset{O}{\underset{OR_{16}}{\overset{\|}{P}}}-O-, \quad R_{16}-\overset{O}{\underset{OR_{16}}{\overset{\|}{P}}}-O-,$$

azido or $L_1$—O—;
$R_2$ is hydrogen or halogen;
$R_3$ is hydrogen, unsubstituted or substituted $C_1$–$C_{10}$alkyl, unsubstituted $C_1$–$C_{10}$alkylcarbonyl, $C_1$–$C_{10}$alkoxycarbonyl or benzyloxycarbonyl;

$R_4$ is hydrogen, unsubstituted or substituted $C_1$–$C_{10}$alkyl, unsubstituted $C_1$–$C_{10}$alkylcarbonyl, $C_1$–$C_{10}$alkoxycarbonyl or benzyloxycarbonyl;
$R_{10}$ is $C_1$–$C_4$alkyl or unsubstituted benzyl or phenyl;
$R_8$ is unsubstituted or substituted $C_1$–$C_{10}$alkyl, $C_2$–$C_{10}$alkynyl or $C_1$–$C_{10}$alkyl-C(Q)—, cyano, $C_1$–$C_{10}$alkoxycarbonyl or $L_2$—NH—$C_1$–$C_{10}$alkyl;
$R_9$ is hydrogen, unsubstituted or substituted $C_1$–$C_{10}$alkyl, $C_1$–$C_{10}$alkyl-C(Q)—, $NH_2$—$SO_2$— or $R_{18}(R_{19})N$—C(Q)—; or
$R_8$ and $R_9$ together form a ring —X—Y—Z—, in which
X is the groups $$-\overset{Q}{\underset{\|}{C}}- \text{ or } -\overset{Q}{\underset{\|}{C}}-C_1-C_3\text{alkylene},$$

wherein
the alkylene chain can be unsubstituted or substituted by hydroxyl or amino;
Q is oxygen;
Y is oxygen or —$NR_5$—;
Z is the groups $$-\overset{Q}{\underset{\|}{C}}- \text{ or } -\overset{Q}{\underset{\|}{C}}-C_1-C_3\text{alkylene},$$

wherein
the alkylene chain can be unsubstituted or substituted by hydroxyl, amino, $C_1$–$C_4$alkylamino, $C_1$–$C_4$alkoxycarbonyl or $C_1$–$C_4$alkylaminocarbonyl;
$R_5$ is hydrogen, unsubstituted $C_1$–$C_{10}$alkylcarbonyl, $C_1$–$C_{10}$alkoxycarbonyl, benzyloxycarbonyl or phenyl;
$R_6$ is $C_1$–$C_4$alkoxycarbonyl;
$R_7$ is hydrogen, unsubstituted or substituted $C_1$–$C_{10}$alkyl or benzyl;
$R_{13}$ is hydrogen or unsubstituted or substituted $C_1$–$C_{10}$alkyl, $C_1$–$C_{10}$alkylcarbonyl, phenyl or benzyl;
$R_{16}$ is $C_1$–$C_5$alkyl, $C_3$–$C_5$alkenyl, phenyl or benzyl;
$R_{18}$ benzyl or benzyloxycarbonyl; and
$R_{19}$ is hydrogen, unsubstituted $C_1$–$C_{10}$alkylcarbonyl or benzyl.

9. A process according to claim 1, wherein, for the cyclization of the compound of the formula XI to give the compound of the formula XII in reaction step a), an aprotic solvent and, as the catalyst, a Lewis or Brönsted acid are used.

10. A process according to claim 9, wherein acetonitrile or nitromethane is used as the aprotic solvent and $CF_3SO_2OSi(CH_3)_3$ or $NH_2$—$SO_3H$ is used as the catalyst.

11. A process according to claim 1 for the preparation of the compound of the formula Ia (Ia)

which comprises a) cyclizing the compound of the formula XIa

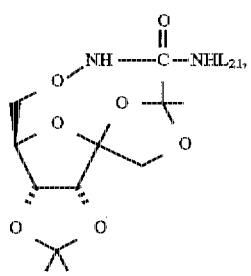

(XI)

in which

L$_{21}$ is hydrogen, benzyl, acetyl, tosyl, 2-nitrobenzyl, 3,4-dimethoxybenzyl or p-methoxybenzyl, with a catalytic amount of a Lewis or Brönsted acid in an aprotic organic solvent to give the compound of the formula XIIa

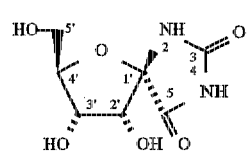

(XIIa)

in which

L$_{21}$ is as defined, and b$_2$) subjecting this compound to further cyclization by reaction with an oxidizing agent and, in the tricyclic compound of the formula VIIIa thus obtained

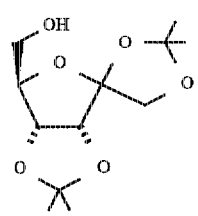

(VIIIa)

splitting off the radical L$_{21}$ by oxidation or reduction, in the compound of the formula XIIIa thus obtained

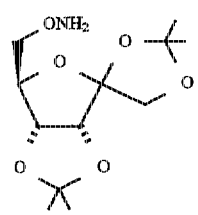

(XIIIa)

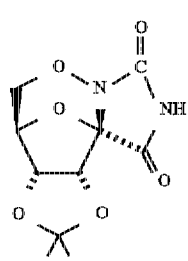

splitting the N—O bond with an organometallic compound or by hydrogenolysis to give the compound of the formula XIVa

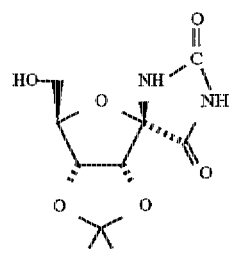

(XIVa)

and subsequently hydrolysing this to remove the isopropylidene protective group.

12. A process for the preparation of the compound of the formula Ia

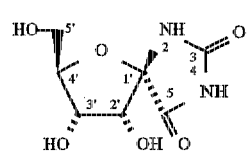

(Ia)

which comprises (1) reacting the compound of the formula IXa

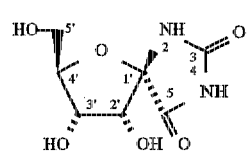

(IXa)

with an N-hydroxyimide and (2) hydrazine hydrate, (3) converting the compound of the formula Xa thus obtained

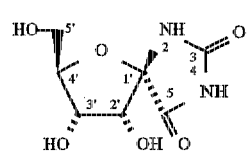

(Xa)

with an isocyanate of the formula IV

L$_2$N=C=O    (IV), in which

L$_{21}$ is hydrogen, benzyl, acetyl, tosyl, 2-nitrobenzyl, 3,4-dimethoxybenzyl or p-methoxybenzyl, into the compound of the formula XIa

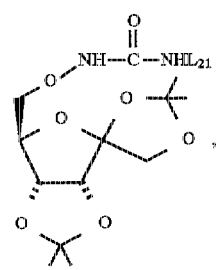

(XIa)

(4) subsequently cyclizing this with a catalytic amount of a Lewis or Brönsted acid in an aprotic organic solvent to give the compound of the formula XIIa

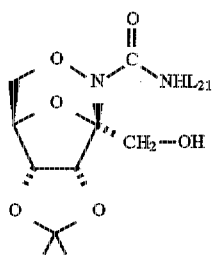
(XIIa)

(5) subjecting this compound to a further cyclization by reaction with an oxidizing agent and (6) in the tricyclic compound of the formula VIIIa thus obtained

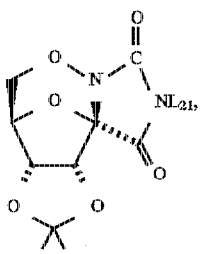
(VIIIa)

wherein in the compounds of the formulae XIa, XIIa and VIIIa the radical $L_{21}$ is as defined, splitting off the radical $L_{21}$ by oxidation or reduction and thus converting the compound into the compound of the formula XIIIa

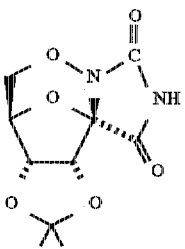
(XIIIa)

(7) in which the N—O bond is split with an organometallic compound or by hydrogenolysis to give the compound of the formula XIVa

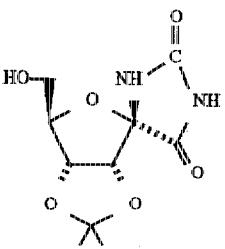
(XIVa)

and (8) subsequently hydrolysing this compound to remove the isopropylidene protective group.

13. A process for the preparation of the compound of the formula Ia

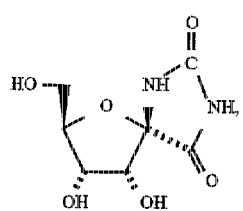
(Ia)

which comprises (9) reacting the compound of the formula IIb

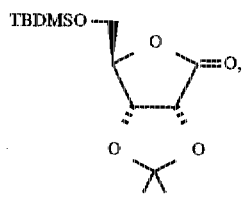
(IIb)

in which

TBDMS is the protective group

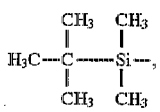

with an acetylide and subsequently with acetic anhydride, and (10) removing the TBDMS protective group, in the compound of the formula IXb thus obtained

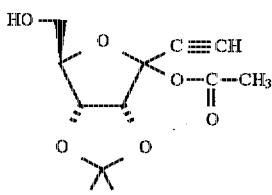
(IXb)

(11) by means of N-hydroxyphthalimide (12) followed by hydrazinolysis, obtaining the alkoxylamine derivate of the formula XIb

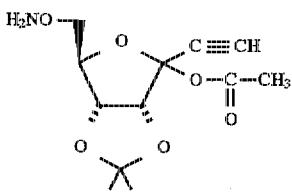
(XIb)

and (4) cyclizing this with a catalytic amount of Lewis or Brönsted acid in an aprotic the compound of the Formula XIIb

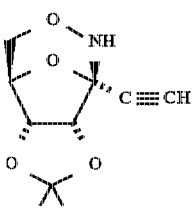
(XIIb)

and (3) converting this with p-methoxybenzyl isocyanate into the compound of the formula XIIe

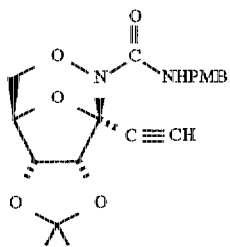
(XIIe)

and (13) subsequently reducing this to give the compound of the formula XIIf

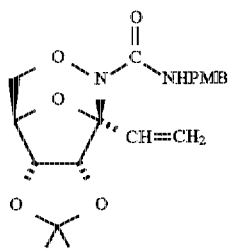
(XIIf)

subjecting the latter compound, (14) after the ozonolysis and reaction with dimethyl sulfide, (15) to a further oxidation to give the compound of the formula VIIIa

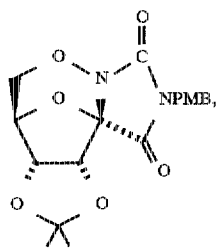
(VIIIa)

wherein in the compounds of the formulae XIIe, XIIf and VIIIa, the PMB radical is the p-methoxybenzyl group, (6) splitting off the radical PMB in the compound of the formula VIIIa with cerium ammonium nitrate and thus converting the compound into the compound of the formula XIIIa

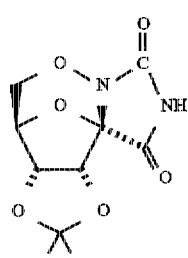
(XIIIa)

(7) in which the N—O bond is split with an organometallic compound or by hydrogenolysis to give the compound of the formula XIVa

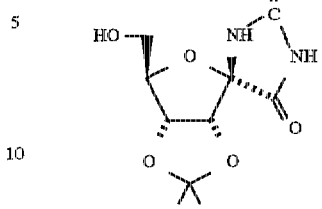
(XIVa)

(8) and subsequently hydrolysing this compound to remove the isopropylidene protective group.

14. A process according to claim 11, wherein, in the compounds of the formulae XIa, XIIa and VIIIa, $L_{21}$ is the p-methoxybenzyl radical.

15. A process according to claim 11, wherein $CF_3SO_2OSi(CH_3)_3$, $BF_3.O(C_2H_5)_2$, $SnCl_4$, $TiCl_4$ or $(C_6H_5)_3C(ClO_4)$ is used as the Lewis acid and $NH_2$—$SO_3H$ or p-toluenesulfonic acid is used as the Brönsted acid.

16. A process according to claim 11, wherein Jones reagent is used as the oxidizing agent in reaction step $b_2$).

17. A process according to claim 11, wherein the radical $L_{21}$ is split off with cerium ammonium nitrate in reaction step $b_2$).

18. A process according to claim 11, wherein the radical $L_{21}$ is split off by reduction with $Na/NH_3$ or by oxidation with 2,3-dichloro-5,6-dicyano-1,4-benzoquinone, boron tribromide or trimethylsilyl iodide in reaction step $b_2$).

19. A process according to claim 11, wherein $Mo(CO)_6$ is used as the organometallic compound in reaction step $b_2$).

20. A process according to claim 11, wherein the hydrogenolytic cleavage of the N—O bond in reaction step $b_2$) is carried out with $H_2$—Ra/Ni.

21. A process according to claim 11, wherein a trifluoroacetic acid/water mixture is used to remove the isopropylidene protective group.

22. A process according to claim 12, wherein p-methoxybenzyl isoycanate or trialkylsilyl isocyanate is used as the isocyanate of the formula IV.

23. A process according to claim 12, wherein, in the compounds of the formulae XIa, XIIa and VIIIa, $L_{21}$ is the p-methoxybenzyl radical.

24. A process according to claim 12, wherein $CF_3SO_2OSi(CH_3)_3$, $BF_3.O(C_2H_5)_2$, $SnCl_4$, $TiCl_4$ or $(C_6H_5)_3C(ClO_4)$ is used as the Lewis acid and $NH_2$—$SO_3H$ or p-toluenesulfonic acid is used as the Brönsted acid.

25. A process according to claim 12, wherein Jones reagent is used as the oxidizing agent in reaction step (5).

26. A process according to claim 12, wherein the radical $L_{21}$ is split off with cerium ammonium nitrate in reaction step (6).

27. A process according to claim 12, wherein the radical $L_{21}$ is split off by reduction with $Na/NH_3$ or by oxidation with 2,3-dichloro-5,6-dicyano-1,4-benzoquinone, boron tribromide or trimethylsilyl iodide in reaction step (6).

28. A process according to claim 12, wherein $Mo(CO)_6$ is used as the organometallic compound in reaction step (7).

29. A process according to claim 12, wherein a trifluoroacetic acid/water mixture is used to remove the isopropylidene protective group.

30. A process according to claim 13, wherein trimethylsilyl-acetylene is used for formation of the acetylide.

31. A process according to claim 13, wherein, for the cyclization of the compound of the formula XIb to give the compound of the formula XIIb in reaction step (4), an aprotic solvent and, as the catalyst, a Lewis or Brönsted acid are used.

32. A process according to claim 31, wherein $CF_3SO_2OSi(CH_3)_3$, $BF_3\text{---}O(C_2H_5)_2$, $SnCl_4$, $TiCl_4$ or $(C_6H_5)_3C(ClO_4)$ is used as the Lewis acid and $NH_2\text{---}SO_3H$ or p-toluenesulfonic acid is used as the Brönsted acid.

33. A process according to claim 32, wherein acetonitrile or nitromethane is used as the aprotic solvent and $CF_3SO_2OSi(CH_3)_3$ or $NH_2\text{---}SO_3H$ is used as the catalyst.

34. A process according to claim 13, wherein $Mo(CO)_6$ is used as the organometallic compound in reaction step (7).

35. A process according to claim 13, wherein the hydrogenolytic cleavage of the N---O bond in reaction step (7) is carried out with $H_2$---Ra/Ni.

36. A compound of the formula XIII

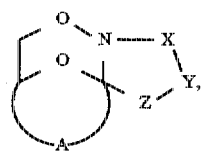

(XIII)

in which
the radicals A, X, Y and Z are as defined in claim 1.

37. A compound of the formula XIII, in which the radicals A, X, Y and Z are as defined in claim 5.

38. A process for the preparation of a compound of the formula XIII

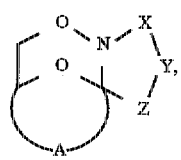

(XIII)

in which
A, X, Y and Z are as defined in claim 1, which comprises
a) cyclizing a compound of the formula XI

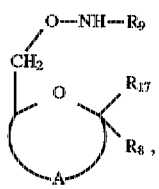

(XI)

in which
A and $R_{17}$ are as defined in claim 1, and
$R_8$ and $R_9$ are as defined in claim 1, with the exception of $C_1$-$C_{10}$alkyl, $C_2$-$C_{10}$alkenyl, $C_2$-$C_{10}$alkynyl, phenyl and benzyl, to give the compound of the formula XII

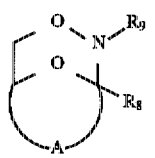

(XII)

and $b_2$) subsequently cyclizing this compound again in a manner known per se to give the compound of the formula XIII.

* * * * *